(12) United States Patent
Rentschler et al.

(10) Patent No.: US 11,089,944 B2
(45) Date of Patent: Aug. 17, 2021

(54) MEDICAL DEVICES INCLUDING TEXTURED INFLATABLE BALLOONS

(71) Applicant: The Regents of the University of Colorado, Denver, CO (US)

(72) Inventors: Mark E. Rentschler, Boulder, CO (US); Karl Johannes, Boulder, CO (US); Steven A. Edmundowicz, Centennial, CO (US)

(73) Assignee: The Regents of the University of Colorado, Denver, CO (US)

( * ) Notice: Subject to any disclaimer, the term of this patent is extended or adjusted under 35 U.S.C. 154(b) by 102 days.

(21) Appl. No.: 16/249,550

(22) Filed: Jan. 16, 2019

(65) Prior Publication Data
US 2019/0216297 A1   Jul. 18, 2019

Related U.S. Application Data

(60) Provisional application No. 62/617,868, filed on Jan. 16, 2018.

(51) Int. Cl.
*A61M 25/10* (2013.01)
*A61M 25/04* (2006.01)
(Continued)

(52) U.S. Cl.
CPC .......... *A61B 1/00082* (2013.01); *A61B 1/273* (2013.01); *A61M 25/1002* (2013.01);
(Continued)

(58) Field of Classification Search
CPC ........... A61B 2017/320048; A61B 17/320725; A61B 17/22032; A61M 2025/1089;
(Continued)

(56) References Cited

U.S. PATENT DOCUMENTS

| 4,364,392 A | 12/1982 | Strother et al. |
| 5,423,745 A * | 6/1995 | Todd ............. A61M 25/1002 |
| | | 604/103.08 |

(Continued)

FOREIGN PATENT DOCUMENTS

| JP | 3799612 B2 | 7/2006 |
| WO | WO 2015/065163 A1 | 5/2015 |
| WO | WO 2018/143254 A1 | 8/2018 |

OTHER PUBLICATIONS

Extended European Search Report, EP16871700.7, dated Jul. 5, 2019.
(Continued)

*Primary Examiner* — Katrina M Stransky
*Assistant Examiner* — Mohammed S Adam
(74) *Attorney, Agent, or Firm* — Polsinelli PC

(57) ABSTRACT

A medical device includes an elongate body and an inflatable balloon attached to and partially surrounding at least a section of the elongate body. The inflatable balloon is selectively inflatable between a deflated state and an inflated state. Engagement between the balloon and a physiological lumen is provided, in part, by multiple protrusions extending from the inflatable balloon and having various physical and functional characteristics. In certain implementations, the balloon may be configured to exhibit various separation forces by applying different strains to the balloon, such as by varying the degree to which the balloon is inflated or deflated.

21 Claims, 16 Drawing Sheets

(51) Int. Cl.
*A61B 1/00* (2006.01)
*A61B 1/273* (2006.01)
*B29D 22/02* (2006.01)

(52) U.S. Cl.
CPC .... *A61M 25/1011* (2013.01); *A61M 25/1029* (2013.01); *A61M 25/04* (2013.01); *A61M 2025/109* (2013.01); *A61M 2025/1015* (2013.01); *A61M 2025/1031* (2013.01); *A61M 2025/1086* (2013.01); *B29D 22/02* (2013.01)

(58) Field of Classification Search
CPC ..... A61M 2025/109; A61M 2025/1086; A61F 2/958; A61F 2/848; A61F 2002/9583; A61F 2002/9586; A61F 2002/8483
See application file for complete search history.

(56) References Cited

U.S. PATENT DOCUMENTS

| | | | |
|---|---|---|---|
| 6,120,516 A | | 9/2000 | Selmon et al. |
| 6,258,099 B1 * | | 7/2001 | Mareiro ................. A61F 2/958 |
| | | | 604/96.01 |
| 6,478,807 B1 | | 11/2002 | Foreman et al. |
| 6,562,049 B1 | | 5/2003 | Norlander et al. |
| 6,676,667 B2 | | 1/2004 | Mareiro et al. |
| 6,835,189 B2 | | 12/2004 | Musbach et al. |
| 6,841,213 B2 | | 1/2005 | Parsonage et al. |
| 7,306,616 B2 | | 12/2007 | Eidenschink et al. |
| 7,354,419 B2 | | 4/2008 | Davies, Jr. et al. |
| 7,459,192 B2 | | 12/2008 | Parsonage et al. |
| 7,776,078 B2 | | 8/2010 | Burgmeier et al. |
| 7,927,362 B2 | | 4/2011 | Shippy, III et al. |
| 7,963,942 B2 | | 6/2011 | Chen |
| 7,985,063 B2 | | 7/2011 | Schewe et al. |
| 8,048,028 B2 | | 11/2011 | Horn et al. |
| 8,048,093 B2 | | 11/2011 | Mapes et al. |
| 8,096,942 B2 | | 1/2012 | Yoshida et al. |
| 8,202,245 B2 | | 6/2012 | Weber et al. |
| 8,216,267 B2 | | 7/2012 | Pallazza |
| 8,353,868 B2 | | 1/2013 | Davies, Jr. et al. |
| 8,550,985 B2 | | 10/2013 | Weber et al. |
| 8,597,239 B2 | | 12/2013 | Gerrans et al. |
| 8,690,824 B2 | | 4/2014 | Holman et al. |
| 8,771,332 B2 | | 7/2014 | Johnson et al. |
| 8,852,146 B2 | | 10/2014 | Horn et al. |
| 8,876,763 B2 | | 11/2014 | Noddin |
| 8,945,047 B2 | | 2/2015 | McAuley et al. |
| 8,945,168 B2 | | 2/2015 | Davies, Jr. et al. |
| 9,067,045 B2 | | 6/2015 | Burton et al. |
| 9,295,808 B2 | | 3/2016 | De Kock et al. |
| 9,339,169 B2 | | 5/2016 | Rentschler et al. |
| 9,409,001 B2 | | 8/2016 | Aggerholm et al. |
| 9,415,193 B2 | | 8/2016 | Campbell et al. |
| 9,492,297 B2 | | 11/2016 | Pallazza |
| 9,521,945 B2 | | 12/2016 | Farhadi |
| 9,592,119 B2 | | 3/2017 | Tilson et al. |
| 9,717,615 B2 | | 8/2017 | Grandt |
| 9,730,726 B2 | | 8/2017 | Bacino et al. |
| 9,867,529 B2 | | 1/2018 | Farhadi |
| 9,901,715 B2 | | 2/2018 | Cully et al. |
| 9,993,626 B2 | | 6/2018 | Lysgaard |
| 10,166,374 B2 | | 1/2019 | Giasolli et al. |
| 10,173,038 B2 | | 1/2019 | Campbell et al. |
| 10,201,683 B2 | | 2/2019 | Schneider et al. |
| 10,335,581 B2 | | 7/2019 | Schneider et al. |
| 10,376,679 B2 | | 8/2019 | Cox et al. |
| 10,456,564 B2 | | 10/2019 | Terliuc et al. |
| 10,617,853 B2 | | 4/2020 | Campbell et al. |
| 2004/0044351 A1 | | 3/2004 | Searle |
| 2004/0092870 A1 * | | 5/2004 | Squire ................. A61M 25/1011 |
| | | | 604/103.08 |
| 2005/0137615 A1 | | 6/2005 | Mapes et al. |
| 2006/0287574 A1 | | 12/2006 | Chin |
| 2007/0106216 A1 | | 5/2007 | Noddin |
| 2008/0228139 A1 * | | 9/2008 | Melsheimer ........ A61M 25/104 |
| | | | 604/103.08 |
| 2008/0269559 A1 | | 10/2008 | Miyamoto et al. |
| 2010/0022832 A1 | | 1/2010 | Makiyama |
| 2010/0240955 A1 | | 9/2010 | Sinai et al. |
| 2010/0318094 A1 | | 12/2010 | Oishi et al. |
| 2012/0289772 A1 | | 11/2012 | O'Connell et al. |
| 2014/0276407 A1 | | 9/2014 | Devries et al. |
| 2015/0057657 A1 | | 2/2015 | Squire et al. |
| 2015/0088246 A1 | | 3/2015 | Astarci et al. |
| 2016/0058982 A1 | | 3/2016 | Aggerholm et al. |
| 2017/0065155 A1 | | 3/2017 | Farhadi |
| 2017/0333075 A1 | | 11/2017 | Bacino et al. |
| 2017/0333686 A1 * | | 11/2017 | Schneider ........... A61M 25/104 |
| 2018/0140804 A1 | | 5/2018 | Tsukamoto et al. |
| 2018/0256863 A1 | | 9/2018 | Lysgaard |
| 2018/0280666 A1 * | | 10/2018 | Yamazaki ........ A61B 17/12109 |
| 2018/0304052 A1 | | 10/2018 | Schneider et al. |
| 2018/0368665 A1 | | 12/2018 | Rentschler et al. |
| 2020/0215310 A1 | | 7/2020 | Rentschler et al. |

OTHER PUBLICATIONS

International Search Report and Written Opinion, PCT/US2016/064915, dated Apr. 13, 2017.
International Search Report and Written Opinion, PCT/US2019/013832, dated Apr. 10, 2019.
International Search Report and Written Opinion, PCT/US2020/033258, dated Aug. 19, 2020.

* cited by examiner

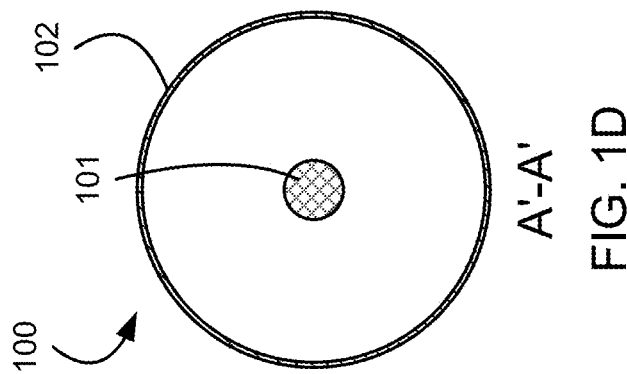
FIG. 1D A'-A'
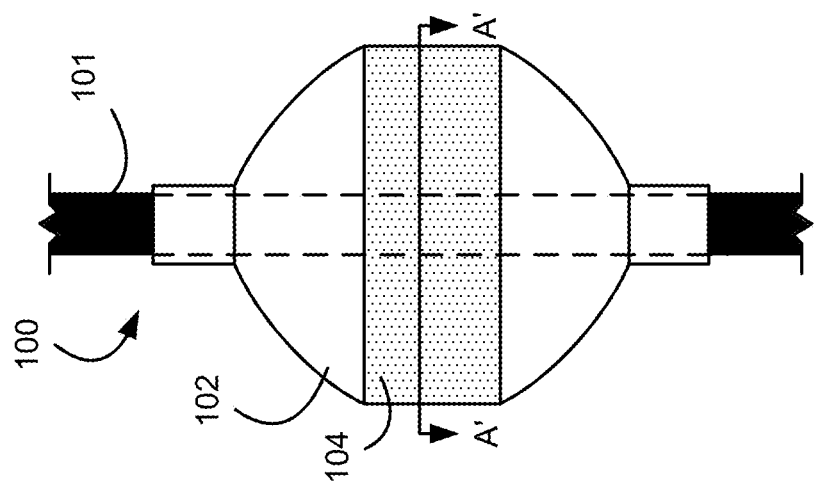
FIG. 1C
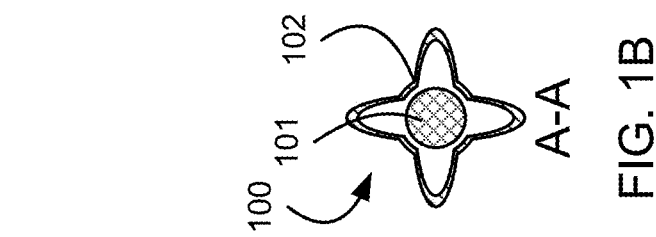
FIG. 1B A-A
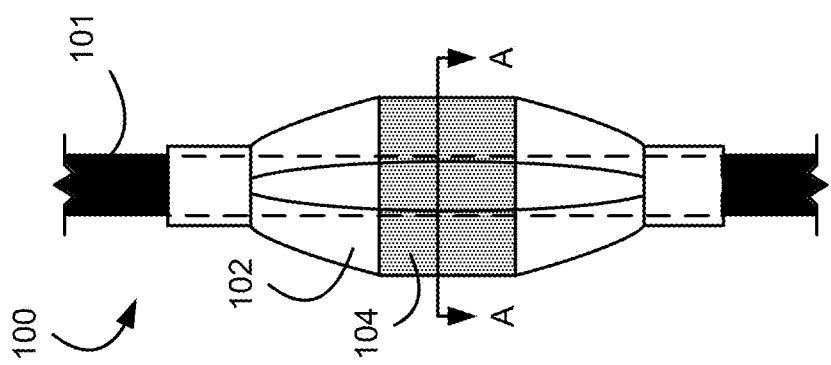
FIG. 1A

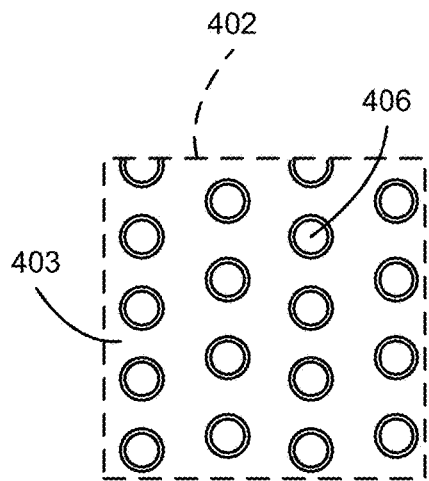
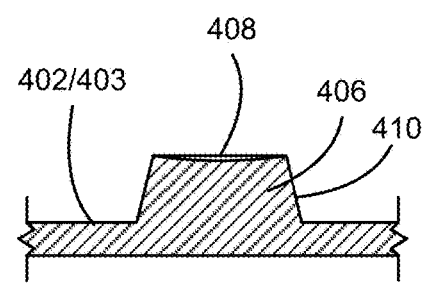
FIG. 4B
FIG. 4A
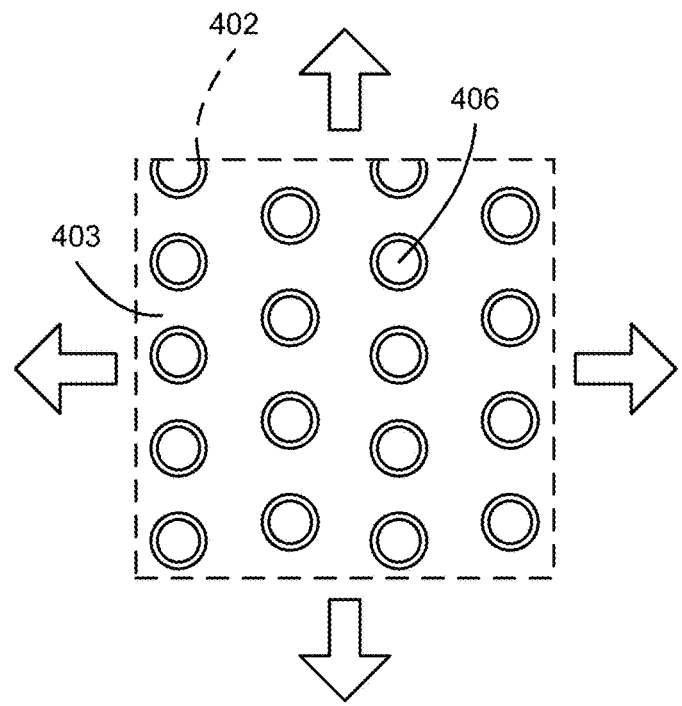
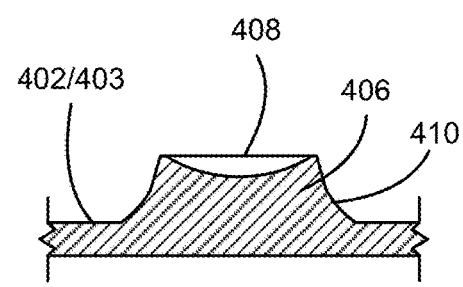
FIG. 5B
FIG. 5A

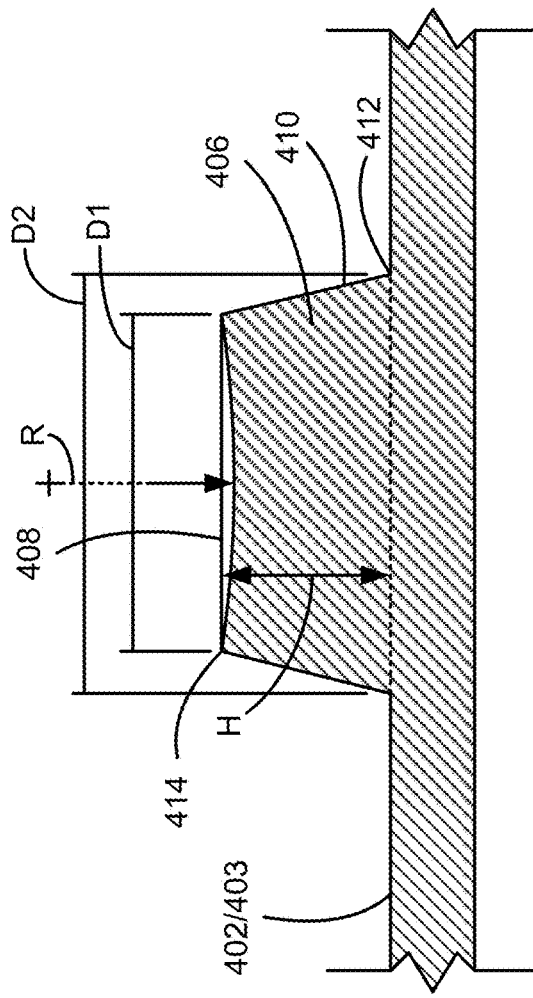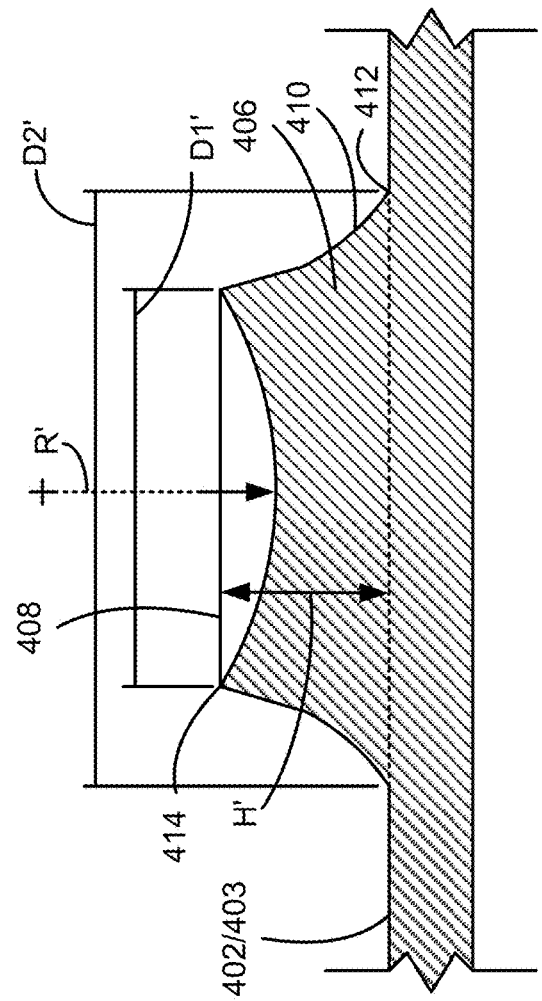

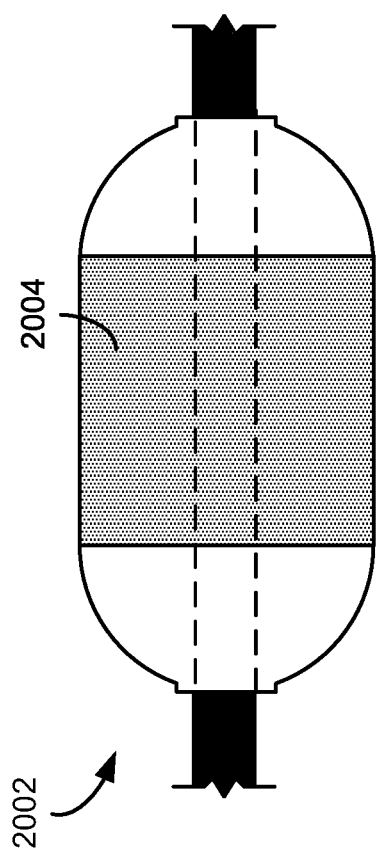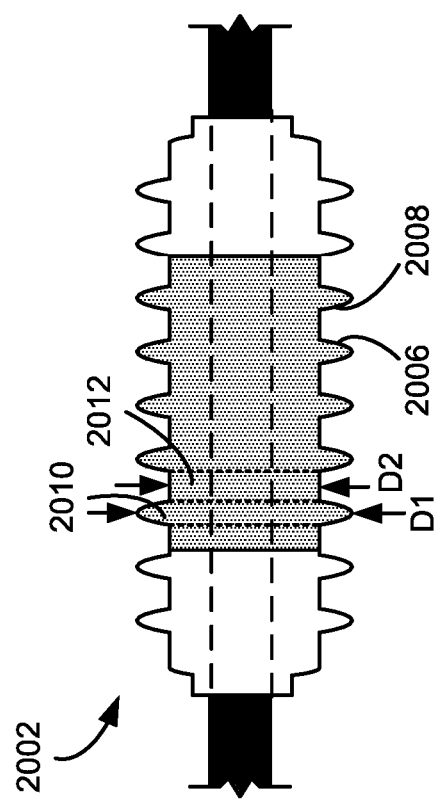

MEDICAL DEVICES INCLUDING TEXTURED INFLATABLE BALLOONS

CROSS-REFERENCE TO RELATED APPLICATION

This application claims the benefit of U.S. Provisional Application No. 62/617,868, filed Jan. 16, 2018, the entirety of which is incorporated herein by reference.

STATEMENT REGARDING FEDERALLY SPONSORED RESEARCH OR DEVELOPMENT

This invention was made with government support under grant number 1636203 awarded by the National Science Foundation. The government has certain rights in the invention.

TECHNICAL FIELD

Aspects of the present disclosure are directed to balloons for use in medical procedures and, in particular, to balloons configured to selectively engage with a physiological lumen such that medical devices including the balloons may be selectively and variably engaged with the lumen.

BACKGROUND

Endoscopy is a procedure wherein a highly trained physician pushes a long flexible endoscope through a physiological lumen of a patient, such as, but not limited to the colon or small bowel. Conventional endoscopes often struggle to complete procedures that involve irregular anatomy or small bowel examination. These factors can lead to missed diagnoses of early state conditions, such as colorectal cancer, which is the third most deadly cancer in America, but which has a 93% survival rate when detected in its initial stages.

To complete many of these examinations, double balloon enteroscopy (DBE) is often used. The double balloon system comprises two balloons, one attached the front of the scope and one attached to a scope overtube. These balloons serve as anchoring points for the endoscope and provide extra support for the long flexible scope to be directed. When these anchoring balloons are inflated and deflated in succession, they aid in the advancement of the scope. When inflated, the balloons push against the wall of the colon, small bowel, or other physiological lumen, and grip the wall forming an anchor point, reducing movement while the scope pushes against the anchor point. DBE has been shown to be a very successful procedure for irregular anatomy patients and small bowel endoscopy.

Balloons commonly used in the art for DBE procedures are conventionally made of smooth latex-like materials. These materials have a low coefficient of friction, especially with the soft, mucous covered wall of the small bowel, colon, and other portions of the gastrointestinal (GI) tract. The low coefficient of friction can cause the balloon to slip prematurely, thus not allowing the scope to properly advance. Over-inflation of the balloons can increase friction with the wall of the small bowel or colon, but at the same time can also cause damage to the patient's GI tract.

There is thus a need in the art for novel devices that can be used to perform gastroenterology and other medical procedures. Such devices should increase the amount of successful completions of such procedures, and provide a more comfortable experience for the patient. By allowing for more colonoscopies to be completed fully, more cases of colorectal cancer would be found in early enough stages for successful treatment.

With these thoughts in mind among others, aspects of the devices and methods disclosed herein were conceived.

SUMMARY

In one aspect of the present disclosure a medical device configured to be inserted into a physiological lumen of a patient, the physiological lumen including a lumen wall. The medical device includes an elongate body and an inflatable balloon attached to and partially surrounding at least a section of the elongate body. The inflatable balloon is selectively inflatable between a deflated state and an inflated state and a plurality of protrusions extend from the inflatable balloon. In one implementation, each of the plurality of protrusions has a height from and including about 5 μm to and including about 1000 μm tall and a stiffness at least equal to the stiffness of the lumen wall.

In certain implementations, the inflatable balloon is formed from at least one of low-density polyethylene, latex, polyether block amide, silicone, poly-siloxane, polyethylene terephthalate, nylon, and polyurethane.

In other implementations, the protrusions may also have a height from and including about 300 μm to and including about 500 μm tall.

In still other implementations, the protrusions may also have a cross-sectional width from and including about 5 μm to and including about 700 μm, including approximately a cross-sectional width of approximately 400 μm.

In certain implementations, the protrusions may be defined by an aspect ratio relating the height and cross-sectional width of the protrusions. For example, in some implementations, the protrusions may have an aspect ratio up to and including about 10, including aspect ratios from and including 0.5 to and including 2.0.

In some implementation, the protrusions may be evenly spaced with a center-to-center spacing from and including about 20 μm to and including about 1,000 μm.

In certain implementations, the protrusions may be integrally formed with the inflatable balloon.

The inflatable balloon may also be one of multiple inflatable balloons distributed along a length of the medical device and the elongate body may include any of an endoscope body, an endoscope overtube, a catheter, and a guide wire.

When in the deflated state a first portion of the balloon may have a first diameter and a second portion of the balloon including at least a portion of the protrusions extends to a second diameter, the second diameter being less than the first diameter. Also, when in the inflated state each of a portion of the protrusions may extend in a respective first direction and, when in the deflated state, each of the portion of the protrusions may extend in a second respective direction, the first respective direction being in a more outwardly radial direction as compared to the second respective direction.

In another embodiment of the present disclosure, a medical device configured to be inserted into a physiological lumen of a patient, the physiological lumen including a lumen wall, is provided. The medical device includes an elongate body and an inflatable balloon attached to and partially surrounding at least a section of the elongate body. The inflatable balloon is adapted to be inflated within the physiological lumen to engage with the lumen wall and to be changed between a first strained state and a second strained state different than the first strained state. The medical device further includes a plurality of protrusions extending from the inflatable balloon. When in the first strained state, a first separation force is required to disengage the inflatable balloon from the lumen wall and, when in the second strained state, a second separation force different than the first state is required to disengage the inflatable balloon from the lumen wall.

In one implementation, changing between the first strained state and the second strained state includes at least one of inflating and deflating the inflatable balloon.

In another implementation, when in the first strained state a first strain is applied to the inflatable balloon and, in the second strained state, a second strain different than the first strain is applied to the inflatable balloon. Each of the first strain and the second strain may be biaxial strains.

In yet another implementation, each of the protrusions may have a first shape having a first surface area when the inflatable balloon is in the first strained state and each of the protrusions may have a second shape having a second surface area when the inflatable balloon is in the second strained state, the first surface area being different than the second surface area. For example, each protrusion may include a respective top surface such that when in the first shape, the top surface has a first concavity and, when in the second shape, the top surface has a second concavity different than the first concavity.

In another embodiment of the present disclosure, a method of advancing a medical device within a physiological lumen wall of a patient is provided. The physiological lumen includes a lumen wall and the medical device includes an elongate body and an inflatable balloon attached to and partially surrounding at least a section of the elongate body. The inflatable balloon is selectively inflatable between a deflated state and an inflated state, and a plurality of protrusions extends from the inflatable balloon. The method includes disposing the medical device within the physiological lumen and translating at least a portion of the medical device including the inflatable balloon along the physiological lumen with the inflatable balloon in a deflated state. The method further includes engaging the inflatable balloon with the lumen wall by inflating the inflatable balloon, where engaging the inflatable balloon with the lumen wall includes engaging at least a portion of the protrusions with the lumen wall. The method also includes modifying a strain on the inflatable balloon to change a separation force required to disengage the inflatable balloon from the lumen wall.

In one implementation, modifying the strain on the inflatable balloon includes at least one of further inflating the inflatable balloon and partially deflating the inflatable balloon.

In other implementations, modifying the strain deforms the protrusions such that the surface area of the protrusions changes as the strain is modified.

BRIEF DESCRIPTION OF THE DRAWINGS

Example implementations of the present disclosure are illustrated in referenced figures of the drawings. It is intended that the implementations and corresponding figures disclosed herein are to be considered illustrative rather than limiting.

FIG. 1A is a side elevation view of a first medical device according to the present disclosure including a balloon in a deflated state.

FIG. 1B is a cross-sectional view of the medical device of FIG. 1A.

FIG. 1C is a side elevation view of the medical device of FIG. 1A in which the balloon is in an inflated state.

FIG. 1D is a cross-sectional view of the medical device of FIG. 1C.

FIG. 4A is a schematic illustration of a textured portion of a balloon according to the present disclosure in a first state of strain.

FIG. 4B is a cross-sectional view of a protrusion of the balloon of FIG. 4A.

FIG. 5A is a schematic illustration of the textured portion of the balloon of FIG. 4A in a second state of strain.

FIG. 5B is a cross-sectional view of the protrusion of FIG. 4B when the balloon of FIG. 4A is in the second state of strain.

FIGS. 6A-6B are more detailed illustrations of the cross-sectional views of FIGS. 4B and 5B.

FIGS. 20A-20B are schematic illustrations of another example balloon in accordance with the present disclosure in each of an inflated state and a deflated state, respectively.

DETAILED DESCRIPTION

Figure 1E:
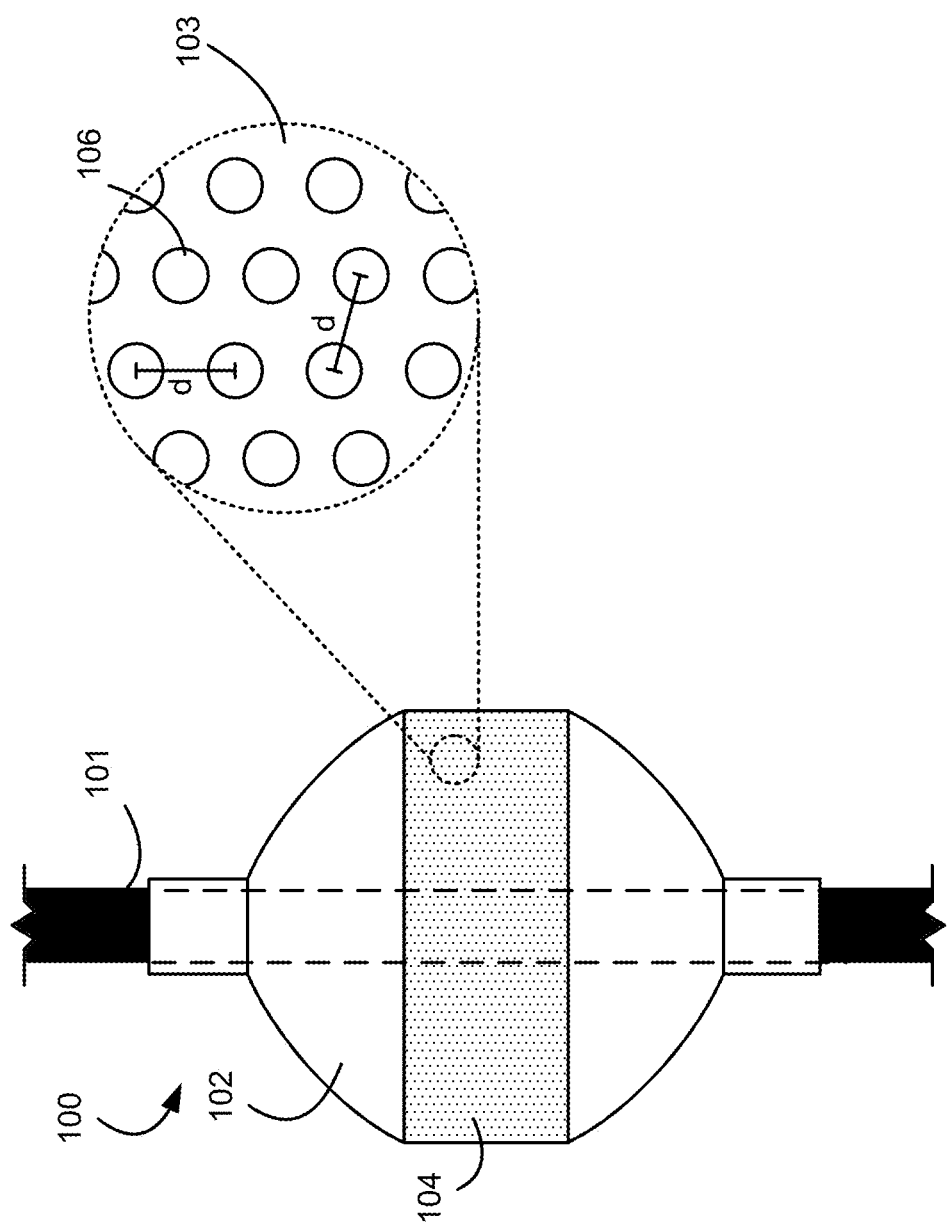
FIG. 1E is a side elevation view of the medical device of FIG. 1A in the inflated state and further including a detail view illustrating protrusions disposed on the balloon.

The current disclosure relates in part to balloon designs that can be incorporated into medical devices, such as endoscopes. In particular, the current disclosure relates to balloons having exterior surfaces that are at least partially textured. Texturing of the balloons is achieved by the inclusion of multiple pillar-like protrusions extending from the surface of the balloon. In at least one application of the current disclosure, a medical device including the balloon is disposed within a physiological lumen with the balloon in a substantially deflated state. The physiological lumen may be a portion of a patient's GI tract, but more generally may be any vessel, airway, duct, tract, stricture, sphincter, biliary stricture, or similar physiological structure. Once positioned within the physiological lumen, the balloon may be inflated such that the protrusions contact the lumen wall, thereby engaging the balloon and medical device with the lumen wall. The balloon may be subsequently deflated to facilitate disengagement of the protrusions from the wall of the lumen, thereby permitting movement of the medical device. Accordingly, the balloons (or similar structures) disclosed herein include textured/patterned surfaces that provide increased friction and adhesion with biological tissue as compared to conventional smooth balloons. As a result of such increased friction and adhesion, balloons in accordance with the present disclosure more reliably engage biological tissue as compared to conventional balloon designs.

As described below in further detail, the shape and distribution of the protrusions may vary in applications of the present disclosure to provide varying degrees of traction between the balloon and the biological tissue with which the balloon is in traction. In certain implementations, the protrusions may also be configured to deform in response to a strain applied to the balloon. Such deformation alters the adhesive and frictional properties of the protrusions. As a result, a physician may control the relative traction of the balloon to the biological tissue by selectively inflating or deflating the balloon. For example, a physician may apply a first strain to the balloon (e.g., by inflating the balloon to a first extent) resulting in a first degree of deformation of the protrusions and a corresponding first engagement level of the balloon (e.g., a first level of engagement based on the adhesive and frictional properties of the protrusions when in a first shape). Subsequently, the physician may apply a second strain (e.g., by modifying the degree to which the balloon is inflated) resulting in a second degree of deformation of the protrusions and a corresponding second engagement level of the balloon.

Although discussed herein primarily in the context of endoscopic balloons for use in the GI tract, the present disclosure may be used in a variety of medical and non-medical applications. Accordingly, to the extent that any particular applications of the present disclosure are discussed herein, such applications should not be viewed as limiting the scope of the present disclosure. Nevertheless example implementations of the present disclosure are discussed below to provide additional details regarding aspects of the present disclosure.

FIGS. 1A-1E are various views of an example medical device 100 including an inflatable balloon 102 in accordance with the present disclosure. More specifically, FIG. 1A is a side elevation view of the medical device 100 with the balloon 102 in an uninflated state, FIG. 1B is a cross-sectional view along cross-section A-A of the balloon 102 of FIG. 1A, FIG. 1C is a side elevation view of the medical device 100 in an at least partially inflated state, FIG. 1D is a cross-sectional view along cross-section A'-A' of the balloon 102 of FIG. 1C, and FIG. 1E is a side elevation view of the medical device 100 including an inlay illustrating a textured portion 104 of the balloon 102.

During use, the medical device 100 may be inserted into and located within a physiological lumen of a patient. Such insertion may generally be performed while the balloon 102 is in the deflated state illustrated in FIG. 1A. Once properly located, air or a similar fluid medium may be provided to the balloon 102 to inflate the balloon, as shown in FIG. 1B. When such inflation is performed with the balloon 102 within the physical lumen, at least a part of the textured portion 104 may be made to abut an inner wall of the physiological lumen, thereby causing frictional and adhesive engagement between the textured portion 104 and the physiological lumen and mucosal lining.

Various arrangements for the balloon 102 on the medical device 100 are feasible. In the specific example of FIGS. 1A-1E, the balloon 102 has a cylindrical body capped by hemi-spherical ends. In another non-limiting example, the balloon 102 is disposed around an endoscope 101 or similar tubular body of the medical device 100 such that the balloon 102 forms a toroidal or spherical shape having a central lumen. In another non-limiting example, the balloon 102 is disposed around the endoscope 101 forming a cylindrical shape having hemi-spherical rounded ends, wherein the endoscope 101 runs along the major axis of the cylinder. In other implementations, the balloon 102 may be ellipsoid in shape or "pill" shaped. Regardless of the foregoing, balloons in accordance with the present disclosure may be substantially any shape as desired.

The balloon 102 may be made of at least one non-rigid material. For example, in one example implementation the balloon material may include one or more of low-density polyethylene (LDPE), latex, polyether block amide (e.g., PEBAX®), silicone, polyethylene terephthalate (PET/PETE), nylon, polyurethane, and any other thermoplastic elastomer, siloxane, or other similar non-rigid materials. In certain implementations, the balloon 102 may be formed from one material; however, in other implementations the balloon 102 may be formed from multiple materials. For example, the balloon 102 may include a body formed from a first material but may also include reinforcing or structural members formed from a second material.

In general, the balloon 102 has a first diameter or shape when in an uninflated state and a second diameter in a minimally inflated state, wherein the second diameter is larger than the first diameter. In certain implementations, the balloon 102 may be further inflatable beyond the minimally inflated state such that the balloon 102 can be further inflated up to a level of maximum strain. For example, in at least one implementation the balloon 102 can be strained up to about 1,000% relative to its uninflated state, although other maximum strain levels are possible. In other implementations, the balloon 102 does not have a set lower inflation limit. The balloon 102 may also be configured to be inflated to a first turgid state having a defined shape and then be further inflated up to a maximum strain while retaining the defined shape.

The balloon 102 may be structured such that, when in the deflated state, the balloon 102 collapses into a particular shape. For example, as illustrated in FIGS. 1A and 1B, the balloon 102 may be configured to collapse into a star or similar shape. Such controlled collapse of the balloon 102 may achieved in various ways including, without limitation, selectively reinforcing portions of the balloon 102 with additional material and including semi-rigid structural elements coupled to or embedded within the balloon 102. In other implementations, the balloon 102 may form a pill, ovoid, or similar elongated shape when deflated, including a shape that substantially corresponds to the inflated shape of the balloon 102.

As illustrated FIG. 1C, the balloon 102 includes at least one textured portion 104. In general and as illustrated in the inlay of FIG. 1C, the textured portion 104 includes multiple protrusions, such as protrusion 106, extending from a surface 103 of the balloon 102. The protrusions 106 of the textured portion 104 may have any pattern. For example and without limitation, the textured portion 104 may include evenly spaced protrusions arranged in a regular geometric pattern, such as a grid. The balloon 102 illustrated in FIG. 1C, for example, includes protrusions arranged in a triangular grid pattern. In other implementations, other grid patterns may be used including, without limitation, square, rectangular, hexagonal, and octagonal grid patterns or any other suitable grid pattern based on a tessellation of geometric shapes. In certain implementations, the textured portion 104 may include multiple areas of protrusions, with each area having a different protrusion density or protrusion pattern. In still other implementations, the protrusions may be arranged in a random or semi-random pattern across the textured portion 104. More generally, textured portions in accordance with implementations of the present disclosure may include any suitable arrangement of protrusions.

In certain implementations, the protrusions 106 may be evenly spaced such that the center-to-center dimension between adjacent protrusions is constant in either the uninflated or inflated state. For example, in one implementation the center-to-center spacing between protrusions (as indicated in the inlay of FIG. 1E by dimension "d") may be about 20 μm to about 1,000 μm in either the uninflated or inflated state. In other implementations, the protrusions may be evenly spaced with a center-to-center spacing from and including about 50 μm to and including about 750 μm apart from one another. In yet another implementation, the protrusions may be evenly spaced with a center-to-center spacing from and including about 100 μm to and including about 600 μm apart from one another.

The protrusions 106 may be formed in various ways. For example and without limitation, the protrusions may be integrally formed with the balloon 102 (e.g., by simultaneously molding the balloon 102 and the protrusions), may be separately formed from and subsequently attached to the balloon 102 (e.g., by first extruding the balloon and then adhering the protrusions to the balloon 102), or may be formed directly onto the balloon 102 (e.g., by a co- or over-molding process in which the balloon 102 is first molded and then the protrusions are molded onto the balloon 102).

As previously discussed, balloons according to the present disclosure may be configured to inflate or deflate in a particular manner. For example, as illustrated in FIG. 1A, the balloon 102 is configured to collapse into a star- or clover-shape when deflated. More specifically, the balloon 102 is configured such that certain longitudinal sections of the balloon 102 are collapsed to a greater degree than others when air is removed from the balloon 102. Such selective collapse may be achieved, for example, by increasing the thickness of the balloon 102 in the longitudinal portions that are to remain protruding when the balloon 102 is deflated.

A similar design is illustrated in FIGS. 20A-20B. More specifically, FIG. 20A illustrates a balloon 2002 in an inflated state while FIG. 20B illustrates the balloon 2002 in a deflated state. Similar to the balloon 102 of FIGS. 1A-1B, the balloon 2002 is configured to selectively collapse when deflated. More specifically, and as illustrated in FIG. 20B, the balloon 2002 is generally divided into alternating axial bands configured to have different diameters when collapsed. For example, a first band 2010 is configured to collapse to a lesser degree (e.g., to a diameter D1) than a second band 2012 (which may collapse, e.g. to a second diameter D2). Stated differently, when in the deflated state, the second band 2012 has a diameter D2 that is less than the diameter D1 of the first band 2010. As previously noted, such selective collapse may be achieved by increasing the thickness of the first band 2010 or by otherwise reinforcing the first band 2010. In other implementations, the shape of at least some of the bands when in the deflated state may be dictated by a mandrel or similar body disposed within the balloon 2002 and about which the balloon 2002 collapses when deflated.

Varying the degree to which the balloon collapses, as illustrated in the examples of FIGS. 1A-1B and 20A-20B, facilitates insertion and transportation of the balloon when in the deflated state. In particular, by reducing the proportion of protrusions that are outwardly/radially facing or otherwise disposed at a maximum diameter, the overall adhesion and friction provided by the balloon is reduced. As a result, the likelihood and amount of contact between the balloon a wall of a physiological lumen is significantly reduced. Referring to FIGS. 20A-20B, for example, the balloon 2002 includes a textured portion 2004 having protrusions according to the present disclosure. When in the inflated state (as shown in FIG. 20A), each of the protrusions is directed substantially outwardly/radially and, as a result, is able to readily contact and engage the wall of the physiological lumen. However, when in the deflated state (as shown in FIG. 20B), sections of the textured portion 2004 of the balloon 2002 (such as faces 2006 and 2008) and their respective protrusions are directed at least partially in a longitudinal direction and, as a result, are less likely to directly engage the wall of the physiological lumen. Similarly, sections of the textured portion 2004 (such as the second band 2012) may be recessed when the balloon 2002 is in the deflated state relative to other sections of the textured portion 2004 (such as the first band 2010). As a result the recessed sections are less likely to contact and engage the wall of the physiological lumen.

Figure 21A:
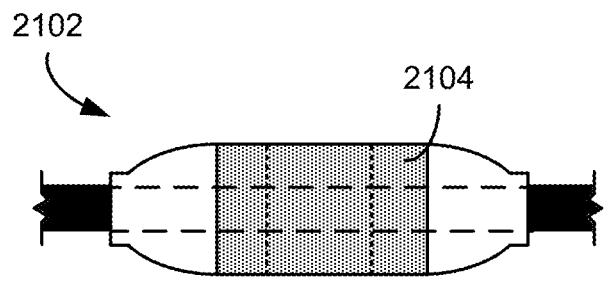
FIGS. 21A-21C are schematic illustrations of yet another example balloon in accordance with the present disclosure in each of a deflated state, a partially inflated state, and an inflated state, respectively.
Figure 21B:
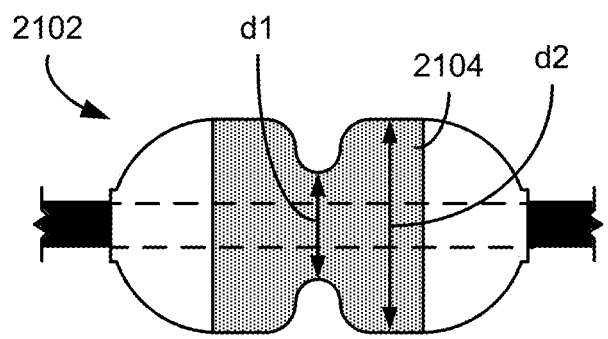
Figure 21C:
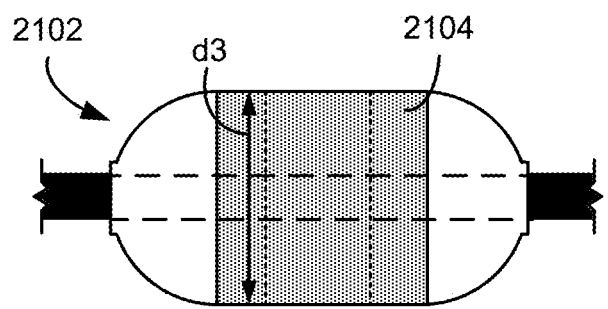

FIGS. 21A-21C illustrates another example balloon 2102 exhibiting non-uniform inflation/deflation. FIG. 21A illustrates the balloon 2102 in a substantially deflated state and in which the balloon 2102 assumes a pill-shaped configuration. As shown in FIG. 21B, the balloon 2102 may be inflated to a first inflation level in which the balloon 2102 assumes an hourglass (or similar shape) in which at least a portion of the balloon 2102 expands to a diameter (d1) that is less than a diameter (d2) of other portions of the balloon 2102. At a second inflation level, the balloon 2102 may expand such that the diameter of the balloon is substantially uniform (d3).

In certain implementations, the controlled inflation of the balloon 2102 may be used to vary the adhesive and frictional force between the balloon 2102 and a wall of a physiological lumen within which the balloon 2102 is disposed. For example, the balloon 2102 includes a textured portion 2104 having protrusions according to the present disclosure. When in the partially inflated state (as illustrated in FIG. 21B), the diameter of the textured portion 2104 varies such that only a limited proportion of the protrusions are each of disposed at the maximum diameter of the balloon 2102 and oriented in an outward/radial direction. As a result, the adhesion and friction between the balloon 2102 and wall of the physiological lumen is reduced as compared to when the balloon 2102 is further inflated (as illustrated in FIG. 21C) such that substantially all of the textured portion 2104 is at the same diameter. Accordingly, a user of the balloon 2102 may inflate the balloon 2102 to the first inflation level to achieve a first degree of engagement and to the second inflation level to achieve a second, greater degree of engagement.

The specific ways in which balloons may be inflated/collapsed described above are provided merely as examples. More generally, balloons in accordance with the present disclosure may be configured to collapse and/or inflate in a non-uniform way. By doing so, different states of deflation/inflation may be used to disposed different proportions of the balloon protrusions at a maximum diameter of the balloon and/or to position different proportions of the protrusions in a substantially outwardly/radially extending direction.

Figure 2A:
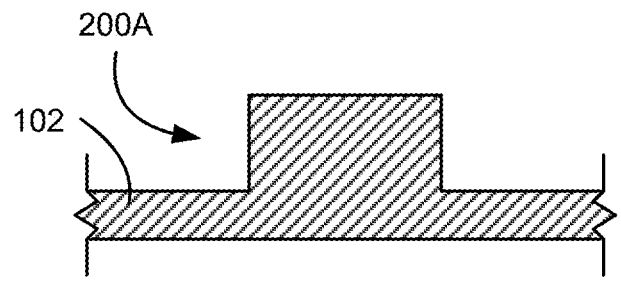
FIG. 2A is a cross-sectional view of a first example protrusion of balloons according to the present disclosure.
Figure 2B:
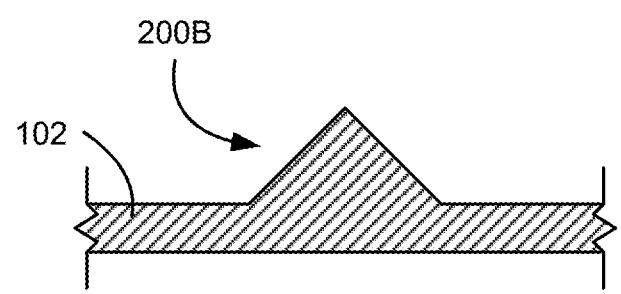
FIG. 2B is a cross-sectional view of a second example protrusion of balloons according to the present disclosure.
Figure 2C:
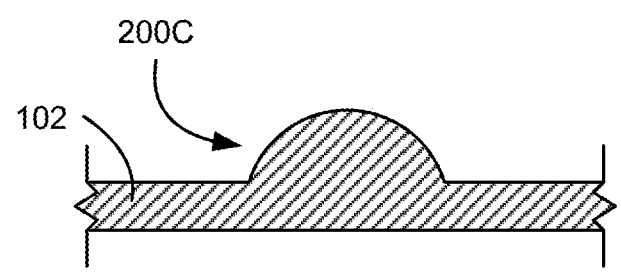
FIG. 2C is a cross-sectional view of a third example protrusion of balloons according to the present disclosure.
Figure 2D:
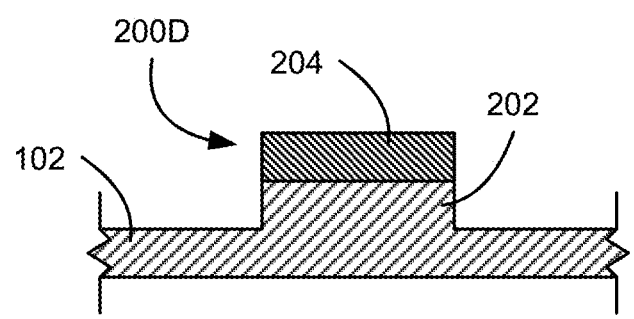
FIG. 2D is a cross-sectional view of a fourth example protrusion of balloons according to the present disclosure.

FIGS. 2A-2D are cross-sections of example protrusions in accordance with the present disclosure. FIGS. 2A-2C in particular illustrate different cross-sectional shapes of example protrusions. In particular, FIG. 2A illustrates a first protrusion 200A extending from the balloon 102 and having a cylindrical or rectangular shape, FIG. 2B illustrates a second protrusion 200B having a triangular or pyramidal shape, and FIG. 2C illustrates a third protrusion 200C having a rounded shape. FIG. 2D is a cross-sectional view of a fourth micro-pillar 200D composed of multiple materials.

The protrusion shapes illustrated in FIGS. 2A-2D are intended merely as examples and other protrusion shapes are possible. For example and without limitation, other implementations of the current disclosure may include protrusions having any shape, including but not limited to rectangular, square, triangular, pentagonal, heptagonal, hexagonal, pyramidal, mushroom, or spherical shape. The ends of the protrusions distal to the surface of the balloon 102 may also be formed in various shapes. For example and without limitation, the distal ends of the protrusions may be flat, rounded (including either of convex or concave), pointed, or mushroomed. The width/diameter of the protrusions may also vary. For example, the distal end of the protrusions may be larger in diameter than the proximal end, so as to resemble a mushroom. In other implementations, the proximal end of the protrusions may be larger in diameter than the distal end, such that the protrusions distally taper.

As noted above, FIG. 2D illustrates a protrusion 200D formed from multiple materials. More specifically, the protrusion 200D includes a first portion 202 proximal the balloon 102 and a second portion 204 distal the balloon 102. As illustrated, the first portion 202 is integrally formed with the balloon 102. The second portion 204, on the other hand, forms a cap or tip of the protrusion 200D that may be coupled to or formed onto the first portion 202 after formation of the first portion 202. In other implementations, each of the first and second portions 202, 204 may be formed from different materials than the balloon 102.

The specific arrangement illustrated in FIG. 2D is intended merely as an example of a multi-material protrusion and other arrangements are possible. For example and without limitation, multi-material protrusions may be formed by embedding or implanting structural elements of a first within protrusions formed of a second material or at least partially encompassing protrusions formed from a first material with a cap, sheath, or similar element formed from a second material. It should also be appreciated that while FIG. 2D illustrates a two-material protrusion 200D, any suitable number of materials may be used to form protrusions in accordance with the present disclosure.

Figure 3:
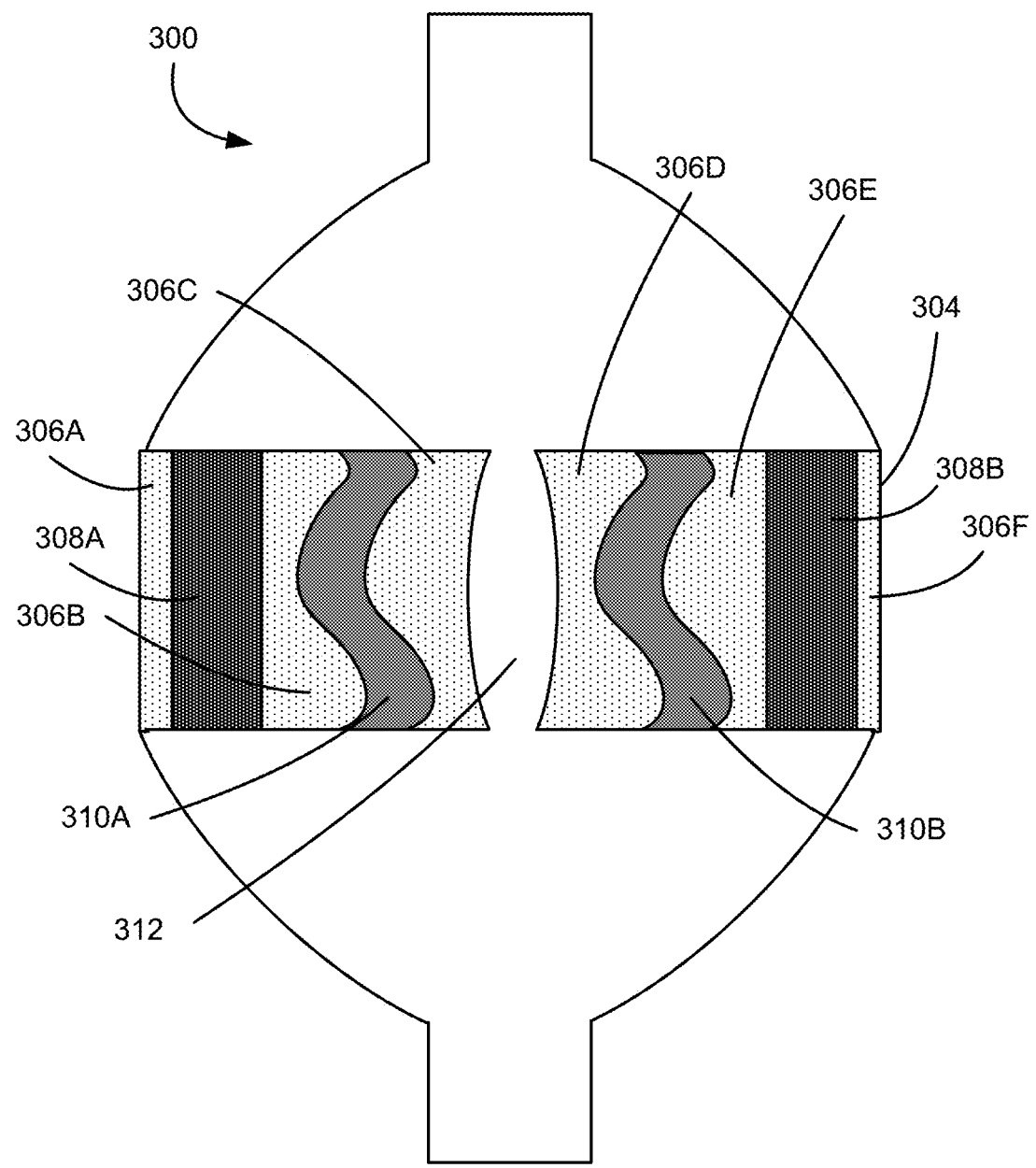
FIG. 3 is a side elevation view of an alternative balloon according to the present disclosure.

The example balloon 102 illustrated in FIGS. 1A-1E included a textured portion 104 having a substantially uniform distribution of protrusions extending therefrom. In contrast, FIG. 3 is a side elevation view of another example balloon 300 in accordance with the present disclosure in a minimally inflated state including a more complicated textured portion 304. More specifically, in contrast to the textured portion 104 of the balloon 102 illustrated in FIG. 1E, which included a substantially uniform pattern and distribution of substantially uniform protrusions, the textured portion 304 includes multiple areas 306A-312 of protrusions. More specifically, the textured portion 304 includes a first set of areas 306A-306F having a relatively low protrusion density; a second set of areas 308A, 308B having a relatively high protrusion density; a third set of areas 310A, 310B having an intermediate protrusion density; and a fourth area 312 that is substantially smooth. Although the areas are described as having different protrusion densities, it should be appreciated that each area may vary in other aspects including, without limitation, one or more of protrusion density, protrusion shape, protrusion rigidity, protrusion distribution pattern, protrusion material, and the like. Similarly, as illustrated in FIG. 3, each area of the textured portion 304 may vary in size and shape.

Referring back to the example medical device 100 of FIGS. 1A-1E, the height of the protrusions 106 may vary in different applications of the present disclosure. For example and without limitation, in at least one implementation the protrusions 106 may be from and including about 5 μm to and including about 700 μm tall when the balloon 102 is in either an uninflated or inflated state. In another implementation, the protrusions may be from and including about 15 μm to and including about 200 μm tall. In yet other implementations, the protrusions may be from and including about 30 μm to and including about 110 μm tall. In at least one specific implementation, the protrusions are from and including about 300 μm to and including about 500 μm to enable the protrusions to penetrate mucosal layers of the physiological lumen. In contrast, in applications in which a mucosal layer may not be present (e.g., cardiac applications), the protrusions may be from and including about 50 μm to and including about 100 μm in height. Specific implementations of the present disclosure may also include protrusions having varying heights. Also, individual protrusions may have different portions extending to different heights (e.g., having a crenellated or other top having varying height).

Similar to height, the cross-sectional width (e.g., the diameter in the case of protrusions having a circular or ovoid cross-section) of each protrusion may vary. For example and without limitation, in one implementation the protrusions have a cross-sectional width from and including about 5 μm to and including about 1000 μm when the balloon 102 is in either the uninflated or inflated state. In another implementation the protrusions have a cross-sectional width from and including about 25 µm to and including about 300 µm. In yet other embodiments the protrusions have a cross-sectional width from and including about 70 µm to and including about 210 µm. In still another implementation the protrusions have a cross-sectional width from and including about 600 µm to and including about 1000 µm. In yet another implementation the protrusions have a cross-sectional width from and including about 300 µm to and including about 500 µm. In another implementation, the protrusions have a cross-sectional width from and including about 150 µm to and including about 250 µm. In at least one specific implementation, the protrusions have a cross-sectional width of about 400 µm. Implementations of the present disclosure may also include protrusions having varying diameters. Also, individual protrusions may have different portions having different diameters (e.g., a tapering shape)

In certain implementations, the overall proportions of a protrusion may instead be defined according to an aspect ratio relating the height of the protrusion to the cross-sectional width/diameter of the protrusion. Although any suitable aspect ratio may be used, in one example implementation, the aspect ratio is less than about 5. In another example implementation, the aspect ratio may be from and including about 0.05 to and including about 10. In yet another example implementation the aspect ratio may be from and including about 0.1 to and including about 5.0. In another example implementation the aspect ratio may be from and including about 0.5 to and including about 1.0. In still another example implementation, the aspect ratio may be from and including about 1.0 to and including about 10.0. In another implementation, the aspect ratio may be from and including about 0.1 to and including about 1. In still another implementation, the aspect ratio may be from and including about 1 to and including about 2. In yet another example implementation, the aspect ratio may be about 0.5, about 1.0, or about 2.0. It should also be appreciated that the aspect ratio for protrusions within a given implementation of the present disclosure may vary such that a first set of protrusions of a balloon conforms to a first aspect ratio while a second set of protrusions for the same balloon conforms to a second aspect ratio. Moreover the cross-sectional width/diameter of the protrusion for purposes of determining an aspect ratio may be any measure of cross-sectional width/diameter. For example, the cross-sectional width/diameter may be the maximum cross-sectional width/diameter of the protrusion, the minimum cross-sectional width/diameter of the protrusion, an average cross-sectional width/diameter of the protrusion, or the cross-sectional width/diameter of the protrusion at a particular location along the length of the protrusion.

The protrusions may also be configured to have a particular stiffness to avoid inadvertent bending or deformation while still allowing engagement of the protrusions with biological tissue. In at least certain implementations, the protrusions are formed such that they have a stiffness that is at least equal to the tissue with which the protrusions. For example, in certain implementations, the stiffness of the protrusions is from and including about 1.0 to and including 2.0 times that of the tissue with which it is to engage. The stiffness may also be expressed as a modulus of elasticity of the material from which the protrusions are formed. For example, in at least some implementations, the protrusions are formed from a material having a modulus of elasticity from and including about 50 kPa to and including about 105 kPa. In other implementations including stiffer protrusions, the protrusions may be formed of a material having a modulus of elasticity from and including about 0.8 MPa to and including about 2.0 MPa.

In certain implementations, protrusions of balloons in accordance with the present disclosure may be configured to deform in response to a strain being applied to the balloon. Such deformation may then be used to dynamically control and adjust traction between the balloon and biological tissue.

FIG. 4A illustrates a portion of a balloon 402 or similar structure in a first state of strain. In certain applications, the first state of strain may correspond to an unstrained state or, alternatively, may correspond to a state in which a first strain is applied to the balloon 402. As shown, the balloon 402 includes multiple protrusions, such as protrusion, 406 distributed across and extending from a surface 403 of the balloon 402. As illustrated in FIG. 4B, the protrusions 406 may, in certain implementations, have a frustoconical shape. FIG. 5A illustrates the portion of the balloon 402 in a second state of strain, in which a strain greater than that of the first state of strain is applied to the balloon 402. As shown in FIG. 5A, in at least some applications, the applied strain when in the second state of strain may be biaxial. Such strain may result, for example, from inflation of the balloon 402. As illustrated in FIG. 5A, the application of strain generally results in both the distance between adjacent protrusions increasing as well as a stretching/deformation of the protrusions. FIG. 5B is a cross-sectional view of the protrusion 406 when a biaxial strain is applied to the balloon 402. As illustrated, the frustoconical shape of the protrusion 406 deforms under the biaxial strain. In particular, each of a top surface 408 and side wall 410 of the protrusion 406 become increasingly concave in response to the application of biaxial strain.

The term "biaxial strain" is generally used herein to refer to a strain applied along two axes which, in certain implementations, may be perpendicular to each other. In certain cases, the biaxial strain may be approximately equal along each axis. For example, strain applied to the balloon may be equal in each of a longitudinal direction and a transverse direction. However, in other implementations, strain may be applied unequally along the axes, including strain resulting in non-uniform deformation of the protrusions (e.g., elongation of compression primarily along a single axis). Moreover, sufficient deformation of the protrusions may also be achieved by application of a uniaxial strain or a multiaxial strain other than a biaxial strain. Accordingly, while the examples described herein are primarily discussed with reference to a biaxial strain resulting in variations in frictional and adhesive engagement resulting from deformation of the protrusion, implementations of the present disclosure are more generally directed to variations in frictional and adhesive engagement from deformation of the protrusions in response to any applied strain.

FIGS. 6A and 6B are cross-sectional views of the protrusion 406 illustrating further details of the protrusion in the strained and unstrained configurations, respectively. As illustrated in FIG. 6A, when in the unstrained configuration, the protrusion 406 has a top diameter (D1) corresponding to the top surface 408 of the protrusion and a base diameter (D2) corresponding to a base 412 of the protrusion 406. The top surface 408 of the protrusion 406 is shown as being disposed at a maximum height (H). The top surface 408 is also shown as being concave and having a concavity defined by a radius of curvature (R). The top surface 408 of the protrusion reaches a height (H) relative to the surface 403 of the balloon 402. It should be appreciated that while the top surface 408 of the protrusion is shown in FIG. 6A as being concave, in other implementations, the top surface 408 may be substantially flat. Also, while the top diameter D1 and base diameter D2 are illustrated in FIG. 6A as being different, in other implementations D1 and D2 may be equal such that the protrusion 406 is substantially cylindrical in shape.

As shown in FIG. 6B, the protrusion 406 may deform in response to a strain applied to the balloon 402. In particular, each of the top diameter (D1) and the base diameter (D2) may expand to a second base diameter (D1') and a second base diameter (D2'), respectively. The radius of curvature (R) of the top surface 408 may also decrease to a second radius of curvature (R'), thereby causing the top surface 408 to become increasingly concave. In addition to the foregoing dimensional changes, the overall height of the protrusion 406 may change from the initial height (H) to a second height (H').

As illustrated in FIGS. 6A and 6B, in at least some implementations of the present disclosure, each protrusion may include a lip or edge 414 at the transition between the side wall 410 and the top surface 408. In general, a relatively sharp lip or edge 414 may allow the protrusions to more readily engage the wall of the physiological lumen and may also facilitate penetration of mucosal or other layers that may be present on the wall. Accordingly, in at least some implementations, the edge/lip 414 may have a radius of no more than about 3 µm.

The initial dimensions of the protrusion 406 may vary. For example, in certain implementations the unstrained upper diameter (D1) of the protrusion may be from and including about 100 µm to and including about 700 µm; the unstrained lower diameter (D2) of the protrusion may be from and including about 100 µm to and including about 750 µm; the unstrained height (H) of the protrusion may be from and including about 100 µm to and including about 700 µm; and the unstrained radius of curvature (R) of the top surface 408 of the protrusion may be from and including about 1 mm to and including about 2 mm. Similarly, in certain implementations, the strained upper diameter (D1') of the protrusion may be from and including about 375 µm to and including about 750 µm; the strained lower diameter (D2') of the protrusion may be from and including about 405 µm to and including about 825 µm; the strained height (H') of the protrusion may be from and including about 200 µm to and including about 400 µm; and the strained radius of curvature (R') of the top surface 408 of the protrusion may be from and including about 500 µm to and including about 750 µm. In one specific example, the D1 may be about 250 µm, D2 may be about 270 µm, H may be about 500 µm, and R may be about 1.5 mm. In the same example, the balloon 402 may be configured to be strained such that D1' can be up to about 375 µm, D2' can be up to about 400 µm; H' may be decreased down to about 450 µm, and R' may be decreased down to about 500 µm. In other implementations, deformation of the protrusion 406 in response to a strain applied to the balloon 402 may instead be based on a change in the surface area of the protrusion 406. For example and without limitation, the balloon 402 may be configured such that the surface area of the protrusion 406 may increase up to about 25%.

During experimental testing, it was observed that separation force between a piece of material including protrusions similar to the protrusion 406 of FIGS. 6A and 6B and a flexible probe simulating biological tissue varied with the degree of biaxial stain applied to the material. More specifically, the probe was first made to contact the material sample, causing the probe to adhere to the material sample. The probe was then withdrawn from contact with the material sample. The force required to affect such separation was measured and observed to vary non-linearly with the degree of biaxial strain applied to the material sample.

Figure 7:
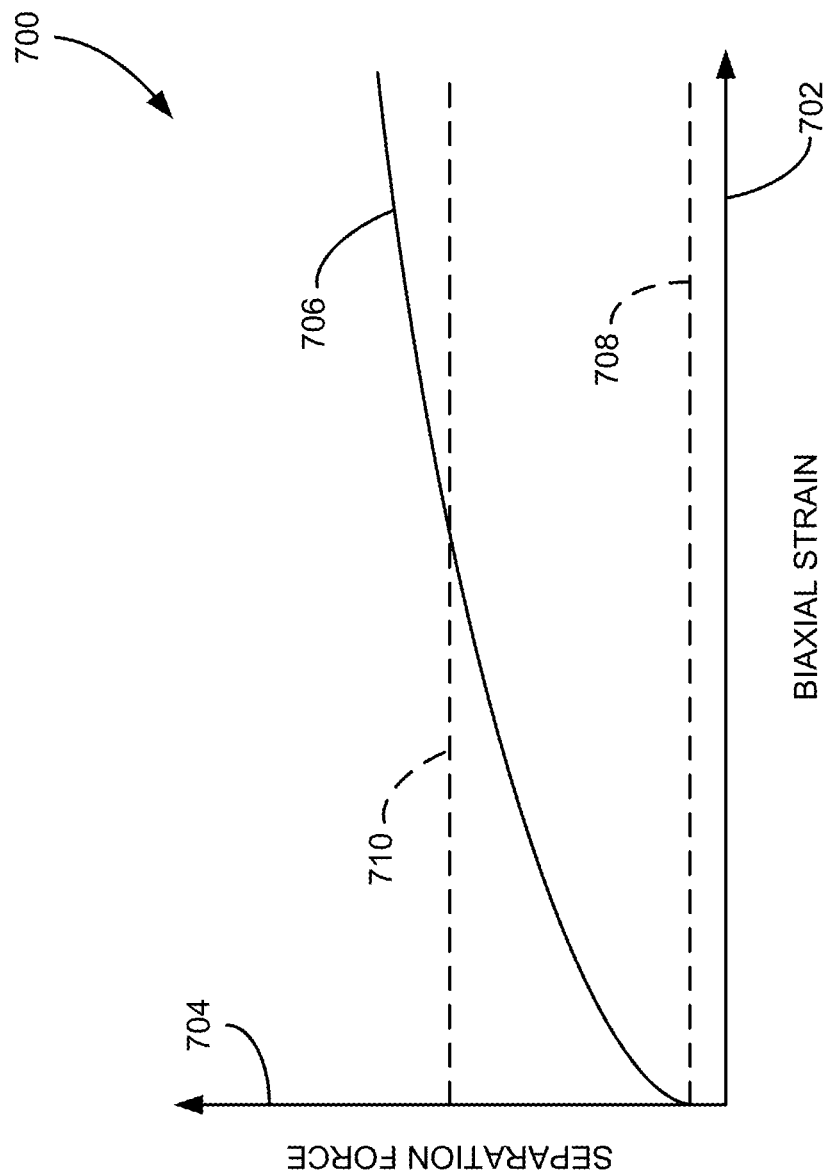
FIG. 7 is a graph illustrating an example relationship between separation force and a strain applied to a balloon in accordance with the present disclosure.

FIG. 7 is a graph 700 summarizing the experimental findings regarding the relationship between separation force and biaxial strain. More specifically, the graph 700 includes a first axis 702 corresponding to biaxial strain and a second axis 704 corresponding to the measured separation force when separating the probe and material sample. As indicated by line 706, the separation force varied in a non-linear fashion in response to changes in biaxial strain.

The graph 700 further indicates a base separation force line 708 corresponding to the separation force when the material sample is unstrained. The graph further includes a "flat" separation force line 710 corresponding to a second material sample substantially similar to the tested material sample but lacking any protrusions.

As illustrated in the graph 700, the separation force for the material having the protrusions may be varied to have a range of values by changing the biaxial strain applied to the material. For example, by applying no or relatively low biaxial strain, the material with protrusions may actually be made to have less separation force (i.e., be made to be less frictional and/or adhesive) than a flat sheet of the same material. However, as biaxial strain is increased friction and adhesion also increase such that, at a certain level of biaxial strain, the separation force of the material including protrusions may be made to exceed that of a flat sheet of the same material.

As shown in the graph 700, this may, in certain implementations, reduce the separation force when unstrained as compared to separation force of a flat material sheet. However, as strain is increased, the separation force may increase above that of the flat sheet. In other words, by selectively applying biaxial strain to the material sample, separation force may be varied, providing physicians with increased control and more reliable engagement for medical devices incorporating balloons in accordance with the present disclosure.

The specific example discussed in FIGS. 4A-7 generally includes protrusions having a flat or partially concave top surface that, when a strain is applied, causes the protrusions to become increasingly concave, thereby increasing their surface area. In other implementations of the present disclosure, the protrusions may instead include a rounded/convex or similar top surface such that when a strain is applied, the top surfaces of the protrusions at least partially flatten. Such flattening may result in a reduction of the surface area and, as a result, a change (generally a reduction) in the separation force between the protrusions and the physiological lumen. Accordingly, whereas in the previous examples a strain is applied to increase protrusion surface area to increase separation force, strain may also be used to decrease protrusion surface area and, as a result, decrease separation force. In either case, however, strain is used as the primary mechanism for altering the shape and the result separation force of the protrusions.

The separation force between the balloon and the physiological lumen may vary across different implementations of the present disclosure and across different states of inflation for any given implementation. However, in at least some implementations, the balloon may be configured to have a separation force less than about 5 N when the balloon is in its deflated state (e.g., as illustrated in FIGS. 1A-1B) to facilitate translation of the balloon along the physiological lumen with minimal adhesion and friction. In other implementations, the separation force when in the deflated state may be less than about 3 N. In a specific example, the separation force in the deflated state may be about 1 N. The balloon may also be configured to have a particular separation force in a minimally inflated state in which the balloon substantially engages the physiological lumen. For example, in at least some implementations, the separation force in the minimally inflated state may be from and including about 10 N to and including about 30 N. In other implementations, the separation force in the minimally inflated state may be from and including about 15 N to and including about 25 N. In one specific implementation, the separation force in the minimally inflated state may be about 20 N.

As previously discussed, in at least some implementations, a strain on the balloon may be applied or modified (e.g., by inflating or deflating the balloon) to modify the adhesive and frictional characteristics of the balloon and, as a result, the separation force between the balloon and physiological lumen. In one implementation, the separation force relative to a minimally inflated state may be reduced to 1% or lower by deflating the balloon and up to and including 200% by overinflating and straining the balloon. In another implementation, the deflated balloon may have a separation force of less than about 5% of the minimally inflated state and a maximum of about 150% by straining the balloon. In still another example implementation, the balloon may have a lower bound separation force of less than about 5% of the minimally inflated state and a maximum of about 125% by straining the balloon. Accordingly, in at least one specific example, the balloon may have a separation force of about 20 N in the inflated state, about 1 N in the deflated state, and about 25 N in a maximum strained state.

Figure 8:
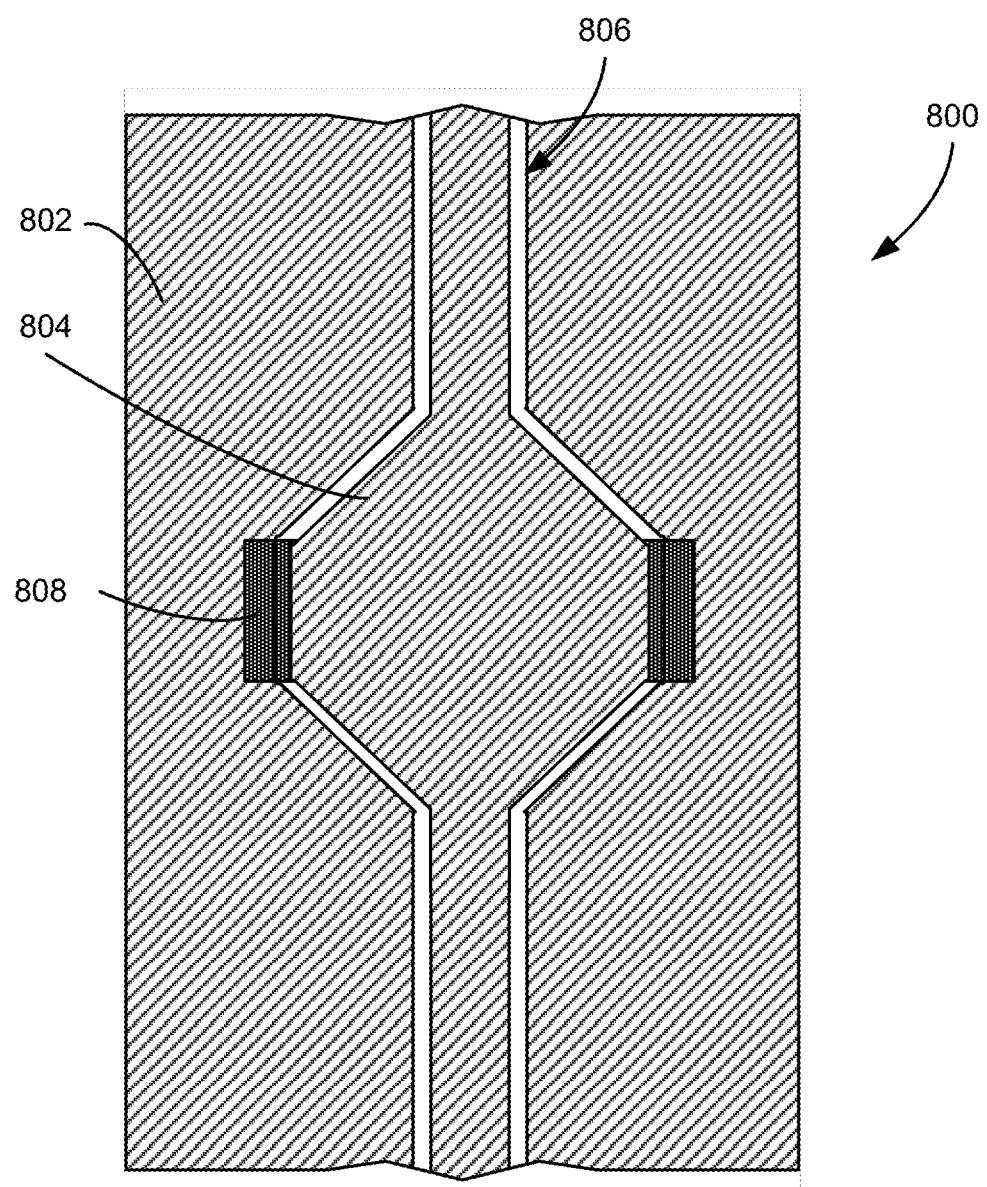
FIG. 8 is a cross-sectional view of a first mold for manufacturing balloons in accordance with the present disclosure.

As previously noted, balloons in accordance with the present disclosure may be manufactured in various ways. For example, in at least one implementation, balloons including protrusions as discussed above may be manufactured through a casting process. FIG. 8 illustrates an example mold 800 for use in such a casting process. As illustrated the mold 800 includes an outer mold piece 802 within which an inner mold piece or core 804 is disposed. The combination of the outer mold piece 802 and the core 804 defines a cavity 806 providing the general shape of the balloon to be molded.

In addition to the outer mold piece 802 and the core 806, the mold 800 includes an insert 808 for forming protrusions on the balloon during casting. The insert 808 is separately formed to have the pattern and distribution of protrusion to be included on the final balloon. The insert 808 may be manufactured in various ways including, without limitation, machining, 3D printing, microlithography, or any other similar manufacturing process. Once formed, the insert 808 may be disposed within and coupled to the outer mold piece 802. In certain implementations, the insert 808 may be formed from a semi-rigid material such as, but not limited to, Kapton 6 or other polyimide material, silicone, latex, or rubber.

During the casting process, balloon material (such as but no limited to ECOFLEX® 50) is poured into the cavity and allowed to set. In certain implementations, a vacuum is also applied to the mold 800 to remove air from the mold cavity 806 and to facilitate the material poured into the cavity 806 to take on the shape of the mold cavity 806, including the protrusions defined by the mold insert 808.

In certain implementations, the overall thickness of the balloon may be modified by changing the thickness of the cavity 806. For example, the outer mold piece 802 may be configured to receive cores of varying sizes such that the thickness of the cavity 806 defined between the outer mold piece 802 and the core 804 may be modified by swapping cores into the mold 800.

Although illustrated in FIG. 8 as having a substantially uniform width, the cavity 806 defined between the outer mold piece 802 and the core 804 may also be non-uniform such that the cavity 806 is wider at certain locations within the mold 800. Accordingly, any balloon formed using the mold 800 will have corresponding variations in its thickness. By varying the thickness of the balloon, various characteristics may be imparted to the balloon. For example, the thickness of certain locations of the balloon may be increased to improve the overall durability and strength of the locations. In other cases, the thickness of the balloon may be varied such that reinforced regions of the balloon are formed that cause the balloon to collapse and/or expand in a particular way. Such reinforced regions may also cause the balloon to assume a particular shape in any of a deflated state, partially inflated state, or fully inflated state.

Figure 9:
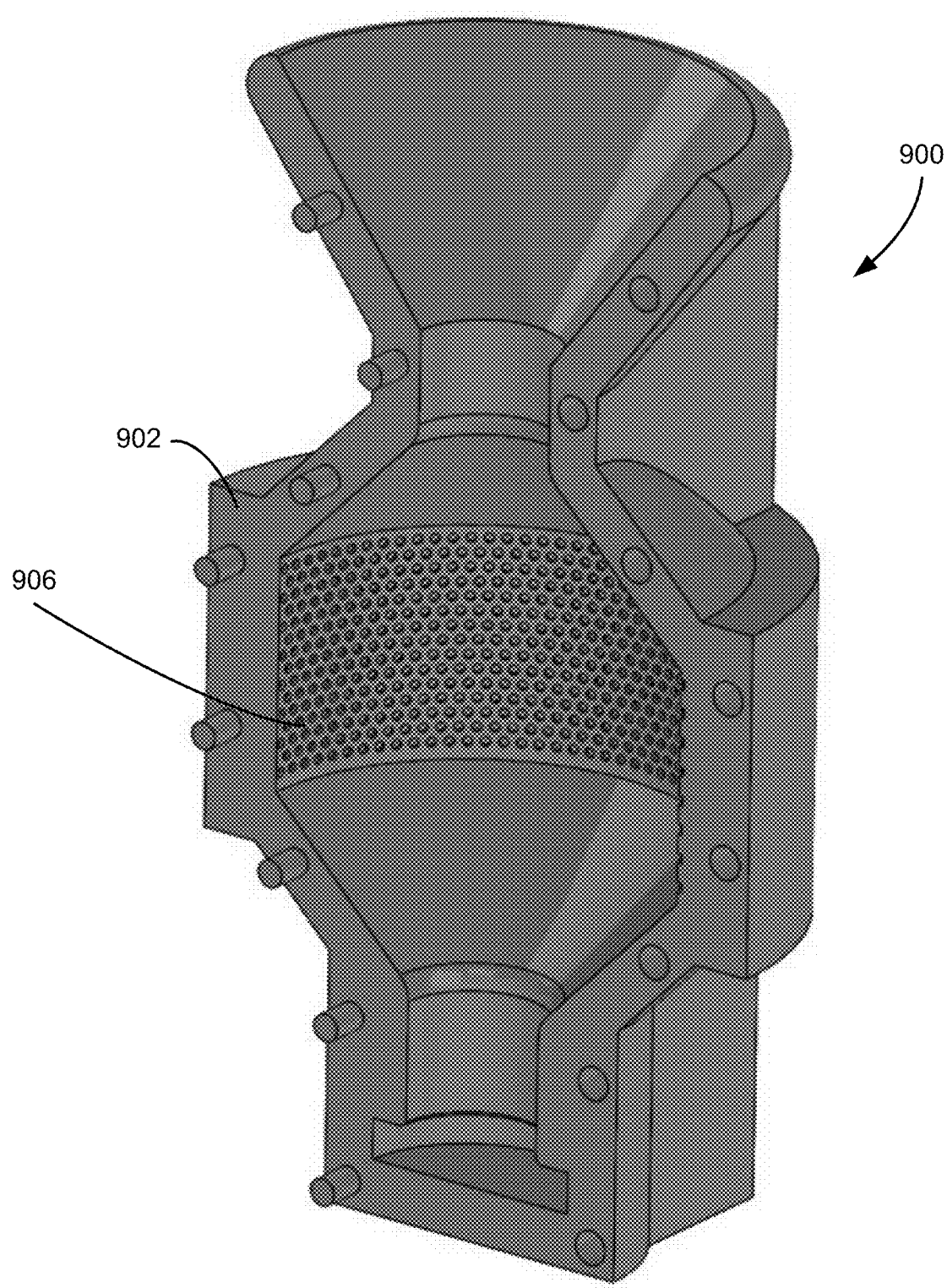
FIG. 9 is an isometric view of a second mold for manufacturing balloons in accordance with the present disclosure.

FIG. 9 is an isometric view of an alternative mold 900 for use in manufacturing balloons in accordance with the present disclosure. The mold 900 includes an outer mold piece 902 within which an inner mold piece or core (not shown) may be disposed. In contrast to the mold 800 of FIG. 8 in which a removable insert 808 is used to form the balloon protrusions, the outer mold piece 902 includes voids 906 formed directly into an inner surface 908 of the outer mold piece 902 that are used to form the protrusions during the casting process.

As discussed above, in at least some implementations, balloons in accordance with the present disclosure may be formed using a casting process. Such casting processes may include piece casting, slush casting, drip casting, or any other similar casting method suitable for manufacturing a hollow article. In a slush casting process, for example, an amount of material may be added to the mold and slushed to coat the internal surface of the mold prior to the material setting. Other fabrication methods may also be implemented including, without limitation, various types of molding (e.g., injection molding) and extrusion processes.

While previous fabrication methods included integrally forming the protrusions with the balloon, in other implementations the protrusions may instead be formed onto a previously formed balloon. For example, in at least one other fabrication method, a base balloon may first be formed. The protrusions may then be formed or coupled to the balloon using a subsequent process. In one example fabrication method, the base balloon is extruded and then the protrusions are then added to the base balloon using a spray method. In another example fabrication method, the base balloon is formed using a first casting or molding process and, once the base balloon is set, a second casting or molding process (e.g., an over-molding process) is applied to form the protrusions on the exterior surface of the base balloon.

As previously discuss in the context of FIGS. 1A-1E, balloons in accordance with the present disclosure may be implemented for use in various medical devices. FIGS. 10-16 are schematic illustrations of various example medical devices and configurations of such medical devices including balloons of the present disclosure. It should be appreciated that the medical devices provided are merely example devices and are therefore non-limiting. More generally, balloons in accordance with the present disclosure may be used in conjunction with any medical device adapted to be inserted into a physiological lumen. In certain implementations, the medical device may include a lumen running its length. The device lumen may serve as a tool or catheter port such that tools and/or catheters can be threaded down the length of the medical device and out of a distal end of the device. Alternatively, the device may be threaded onto tools or catheters already disposed within the physiological lumen.

Figure 10:
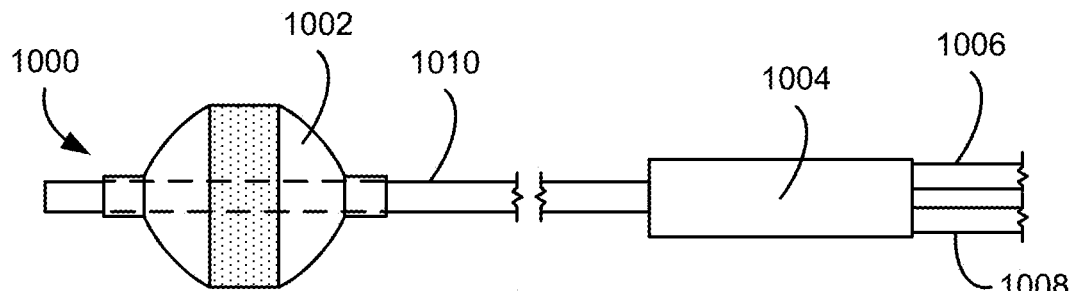
FIG. 10 is a schematic illustration of a medical device in the form of a catheter delivery tool in accordance with the present disclosure.

FIG. 10 is a schematic illustration of a first medical device 1000 in the form of a catheter delivery tool. As illustrated, the medical device 1000 includes a proximal hub 1004 from which each of a catheter tool channel 1006 and a balloon insufflation channel 1008. A distal portion 1010 of the catheter tool channel 1006 extends from the hub 1004 and includes a balloon 1002 that may be selectively inflated and deflated by providing air to or allowing air to escape from the balloon 1002 via the balloon insufflation channel 1008, respectively. Accordingly, the distal portion 1010 may be inserted into a physiological lumen of a patient with the balloon deflated. Once located at a point of interest within the physiological lumen, air may be provided to the balloon 1002 via the balloon insufflation channel 1008 to cause the balloon 1002 to expand and engage the wall of the physiological lumen. When so engaged, the catheter tool channel 1006 may be used to provide a clear and direct pathway to the location of interest.

The medical device 1000 is described above as being used in conjunction with or to guide a catheter or guide wire within the physiological lumen; however, in other implementations of the present disclosure, balloons in accordance with the present disclosure may be incorporated into catheters or guide wires. For example and without limitation in at least one implementation of the present disclosure an inflatable balloon as described herein may be disposed along a guide wire or catheter (e.g., at or near distal end of the guide wire or catheter). In such implementations, the guidewire or catheter may be inserted into a physiological lumen with the balloon in the deflated state. The balloon may be subsequently inflated to engage the physiological lumen and at least partially anchor the guide wire or catheter within the physiological lumen.

Figure 11:
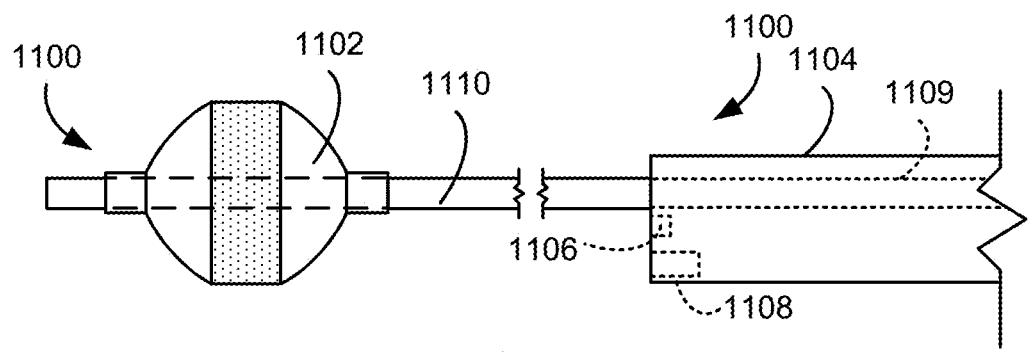
FIG. 11 is a schematic illustration of an example endoscopic medical device in accordance with the present disclosure and including a catheter-mounted balloon.

FIG. 11 is a schematic illustration of a second medical device 1100, which may be an endoscopic device. The second medical device 1100 includes an endoscope body 1104 that may include, for example and without limitation, a light emitting diode (LED) 1106 and a camera 1108. The endoscope body 1104 may also define a catheter channel 1109 through which a catheter 1110 may be inserted. As illustrated in FIG. 11, the catheter 1110 may include a distal balloon 1102 that may be used to at least partially secure the catheter 1110 within a physiological lumen.

In one example application of the medical device 1100, the catheter 1110 may be used as a guide for the endoscope body 1104. More specifically, during a first process the catheter 1110 may be delivered to a point of interest along a physiological lumen with the balloon 1102 in an uninflated state. Once located, the balloon 1102 may be inflated to engage the balloon 1102 with the lumen and at least partially secure the catheter within the lumen. The endoscope body 1104 may then be placed onto the catheter 1110 such that the endoscope body 1104 may be moved along the catheter 1110, using the catheter as a guide.

Figure 12:
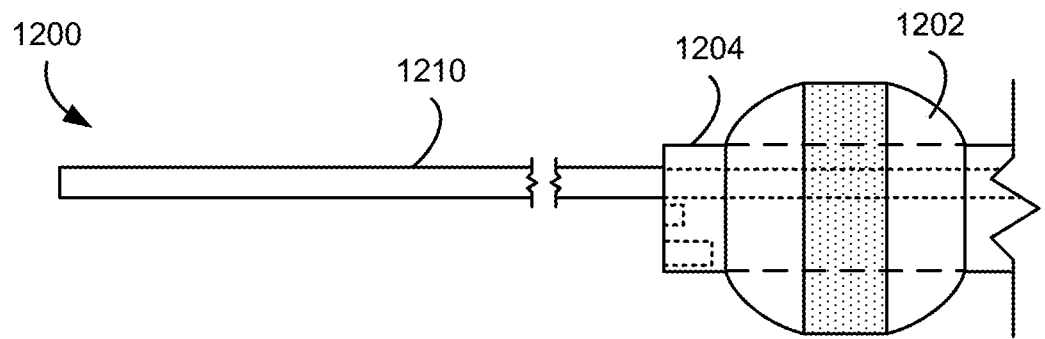
FIG. 12 is a schematic illustration of a second example endoscopic medical device in accordance with the present disclosure and including an endoscope-mounted balloon.

FIG. 12 is a schematic illustration of a third medical device 1200. Similar to the medical device 1100 of FIG. 11, the medical device 1200 includes an endoscope body 1204 (or body of a similar tool) that may be configured to receive a catheter 1210. However, in contrast to the medical device 1100 of FIG. 11 in which the balloon 1102 was coupled to the catheter 1110, the medical device 1200 includes a balloon 1202 coupled to the endoscope body 1204 and which may be used to at least partially secure the endoscope body 1204 within a physiological lumen of a patient.

Figure 13:
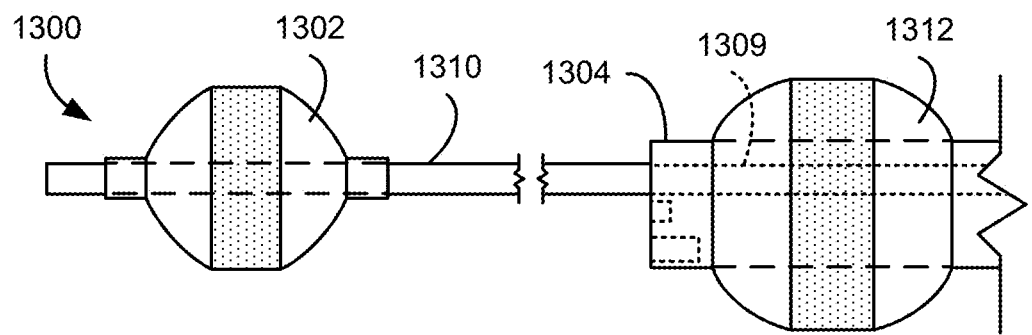
FIG. 13 is a schematic illustration of a third example endoscopic medical device in accordance with the present disclosure and including each of a catheter-mounted balloon and an endoscope-mounted balloon.

FIG. 13 is a schematic illustration of a fourth medical device 1300 that combines aspects of both the medical device 1100 of FIG. 11 and the medical device 1200 of FIG. 12. More specifically, the medical device 1300 includes an endoscope body 1304 that defines a catheter channel 1309 through which a catheter 1310 may be inserted. Like the medical device 1100 of FIG. 11, the catheter 1310 includes a distal balloon 1302 that may be used to at least partially secure the catheter 1310 within a physiological lumen. Also, like the medical device 1200 of FIG. 12, the endoscope body 1304 also includes a balloon 1312.

Figure 17:
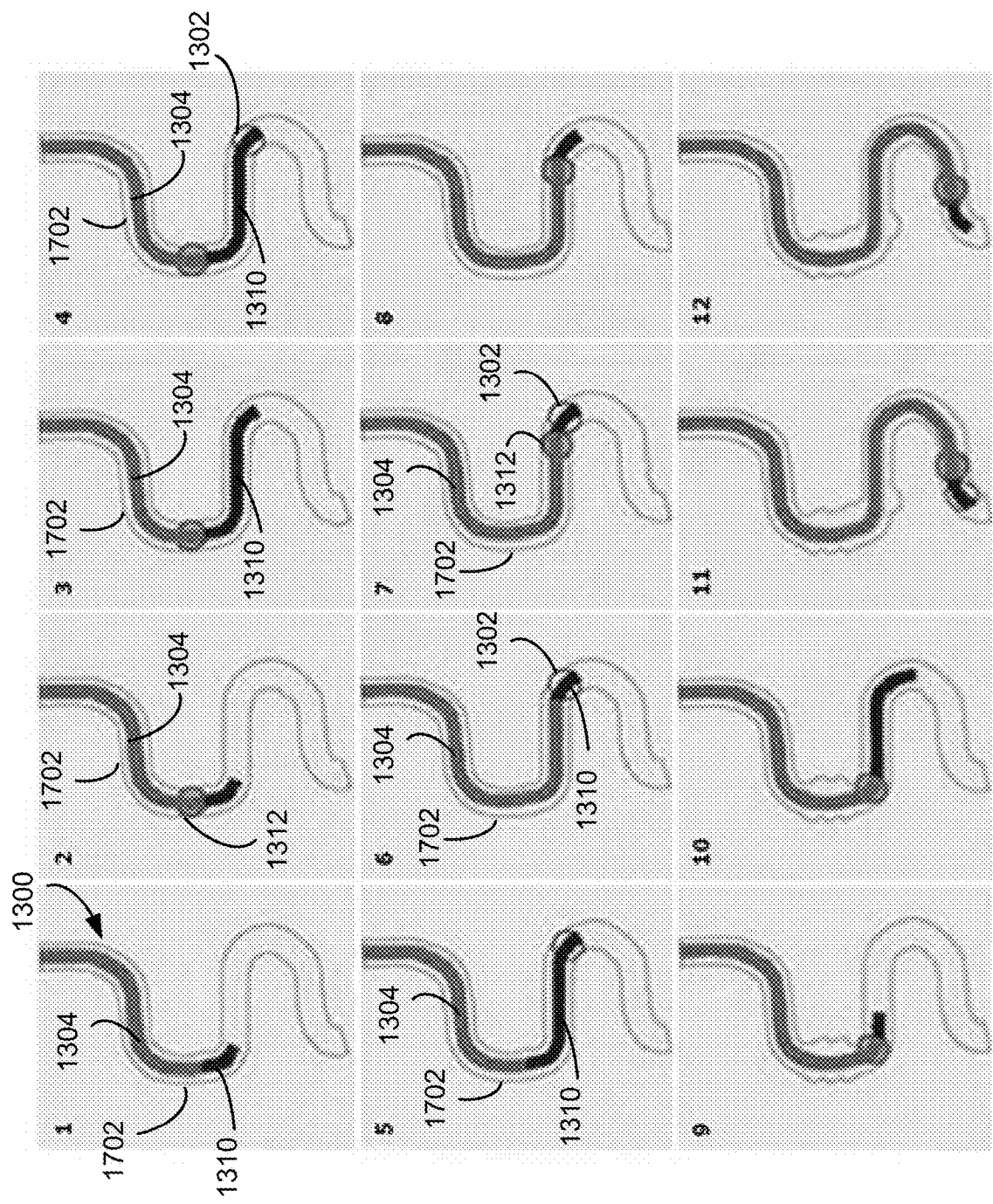
FIG. 17 is a graphical illustration of an example medical procedure performed using the medical device of FIG. 13.

The two-balloon configuration of the medical device 1300 may be used to progress the medical device 1300 along the physiological lumen. For example, FIG. 17 provides a series of illustrations depicting progression of the medical device 1300 along a physiological lumen 1702 (indicated in Frame 1). As illustrated, the medical device 1300 may first be inserted into the physiological lumen in an uninflated/disengaged configuration (Frame 1). The endoscope balloon 1312 may then be inflated to engage the balloon 1312 with the lumen 1702 and to at least partially secure the endoscope body 1304 within the lumen 1702 (Frame 2). With the endoscope body 1304 secured, the catheter 1310 may then be extended from the endoscope body 1304 along the lumen (Frame 3) and the catheter balloon 1302 may be engaged with the lumen 1702 at a second location by inflating the catheter balloon 1302 at the second location (Frame 4). The endoscope balloon 1312 may then be deflated (Frame 5) and the endoscope body 1304 may be progressed along the lumen 1702 using the anchored catheter 1310 as a guide (Frame 6). When the endoscope body 1304 reaches the catheter balloon 1302, the endoscope body 1304 may again be secured within the lumen 1702 by inflating the endoscope body balloon 1312 (Frame 7). As illustrated in Frames 8-12, this process may be repeated to progress the medical device 1300 along the physiological lumen 1702.

In certain implementations, the medical device may be a double balloon endoscope comprising a flexible overtube, as described in PCT Application Publication WO 2017/096350, wherein at least a portion of the outer surface of one or both of the first and second inflatable balloons comprises a micro-patterned surface as described herein. In other embodiments, the endoscope does not comprise an overtube.

Figure 14:
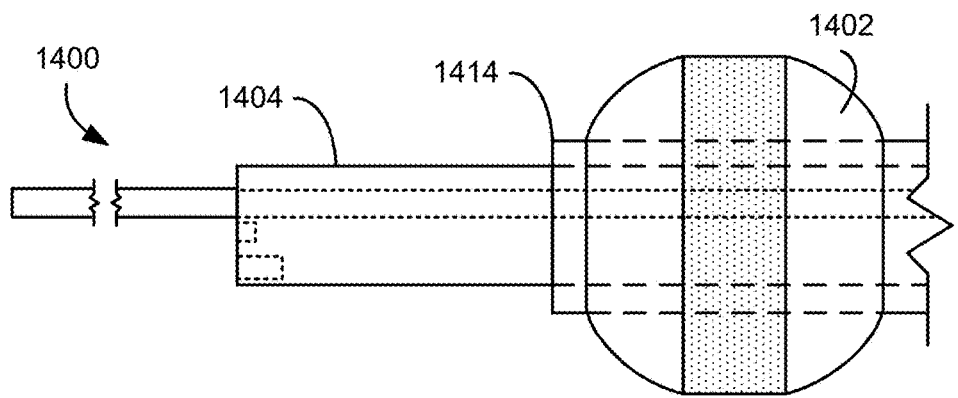
FIG. 14 is a schematic illustration of a fourth example endoscopic medical device in accordance with the present disclosure and including an overtube-mounted balloon.
Figure 15:
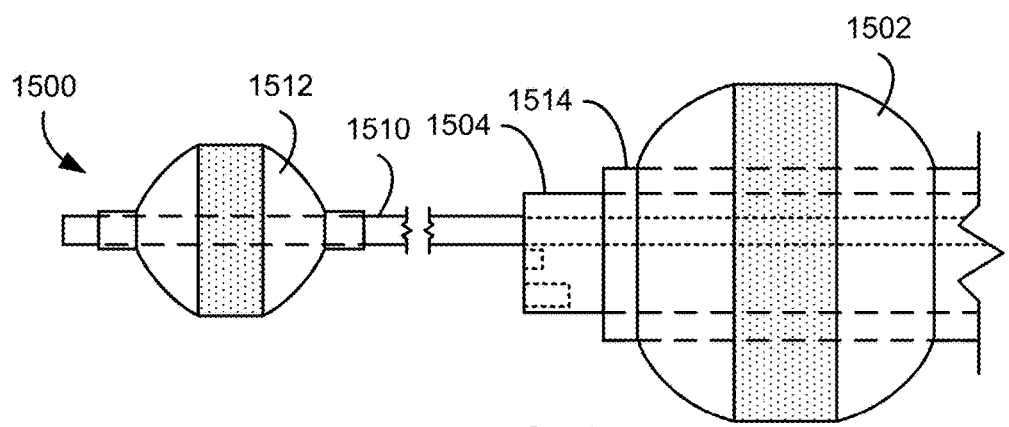
FIG. 15 is a schematic illustration of a fifth example endoscopic medical device in accordance with the present disclosure and including each of a catheter-mounted balloon and an endoscope-mounted balloon.
Figure 16:
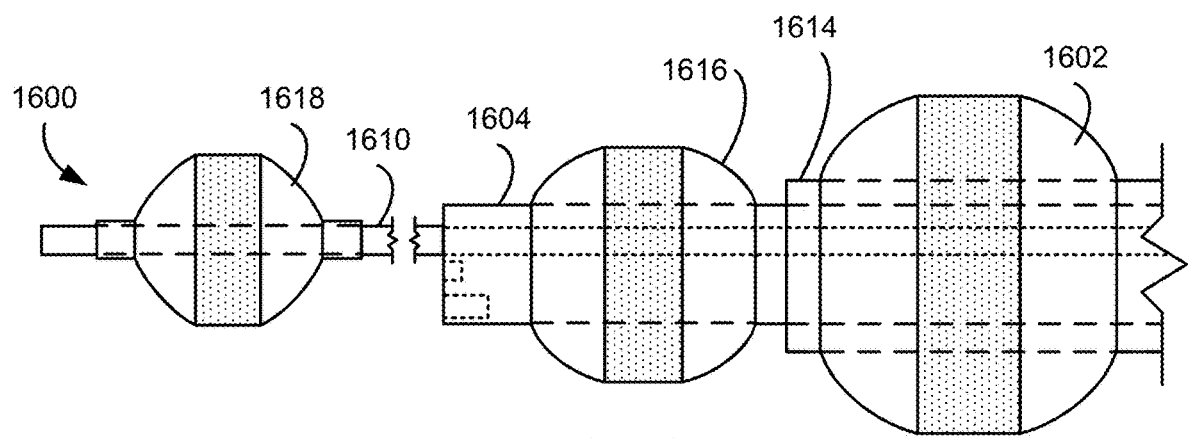
FIG. 16 is a schematic illustration of a sixth example endoscopic medical device in accordance with the present disclosure and including each of a catheter-mounted balloon, an endoscope-mounted balloon, and an overtube-mounted balloon.

FIGS. 14-16 illustrate additional variations of the foregoing example medical devices. FIG. 14 is a schematic illustration of a medical device 1400 in which a balloon 1402 is coupled to an overtube 1414 through which an endoscope device 1404 may be inserted. FIG. 15 is a schematic illustration of a medical device 1500 similar to that of FIG. 14 in that it includes a balloon 1502 coupled to an overtube 1514 through which an endoscope body 1504 extends. In addition to the overtube balloon 1502, the medical device 1500 includes a catheter balloon 1512 coupled to a distal end of a catheter 1510 extending through the endoscope body 1504. An example double balloon endoscope device similar to that of FIG. 15 and including a flexible overtube is described in detail in PCT Application Publication WO 2017/096350, which is incorporated herein by reference in its entirety. Finally, FIG. 16 is another schematic illustration of a medical device 1600 including three distinct balloons. Specifically, the medical device 1600 includes a first balloon 1602 coupled to an overtube 1614, a second balloon 1616 coupled to an endoscope body 1604 extending through the overtube 1614, and a third balloon 1618 coupled to a catheter 1610 extending from the endoscope body 1604.

In each of the medical tools, it is assumed that the described devices include suitable channels for delivering air or other fluid to the disclosed balloons to inflate the balloons and for removing air/fluid from the balloons to deflate the balloons. For example, each device may include a proximal manifold or coupling that may be connected to a pump or other fluid supply and that further includes a vent or return channel through which fluid may be removed from the balloons. In certain implementations, the medical device includes tubing that is in fluidic communication with one or more balloons of the device, the tubing allowing for controlled inflation and/or deflation of one or more of the balloons. In implementations in which the medical device includes multiple balloons, the tubing used to inflate one or more of the multiple balloons. Alternatively, different sets of tubing may be used to independently control inflation and deflation of respective subsets of the balloons of the medical device.

It should also be appreciated that in implementations of the present disclosure having multiple balloons, only one balloon need to have protrusions in accordance with the present disclosure. In other words, medical devices in accordance with the present disclosure my include one textured balloon as described herein, but may also include any number of non-textured balloons or balloons having designs other than those described herein. Moreover, while the example medical devices of FIGS. 10-17 illustrate balloons located near the distal end of components of the medical devices (e.g., catheters, endoscope bodies, overtubes), in other implementations, balloons may be disposed at any location along such components, including at multiple locations along a given component.

Figure 18:
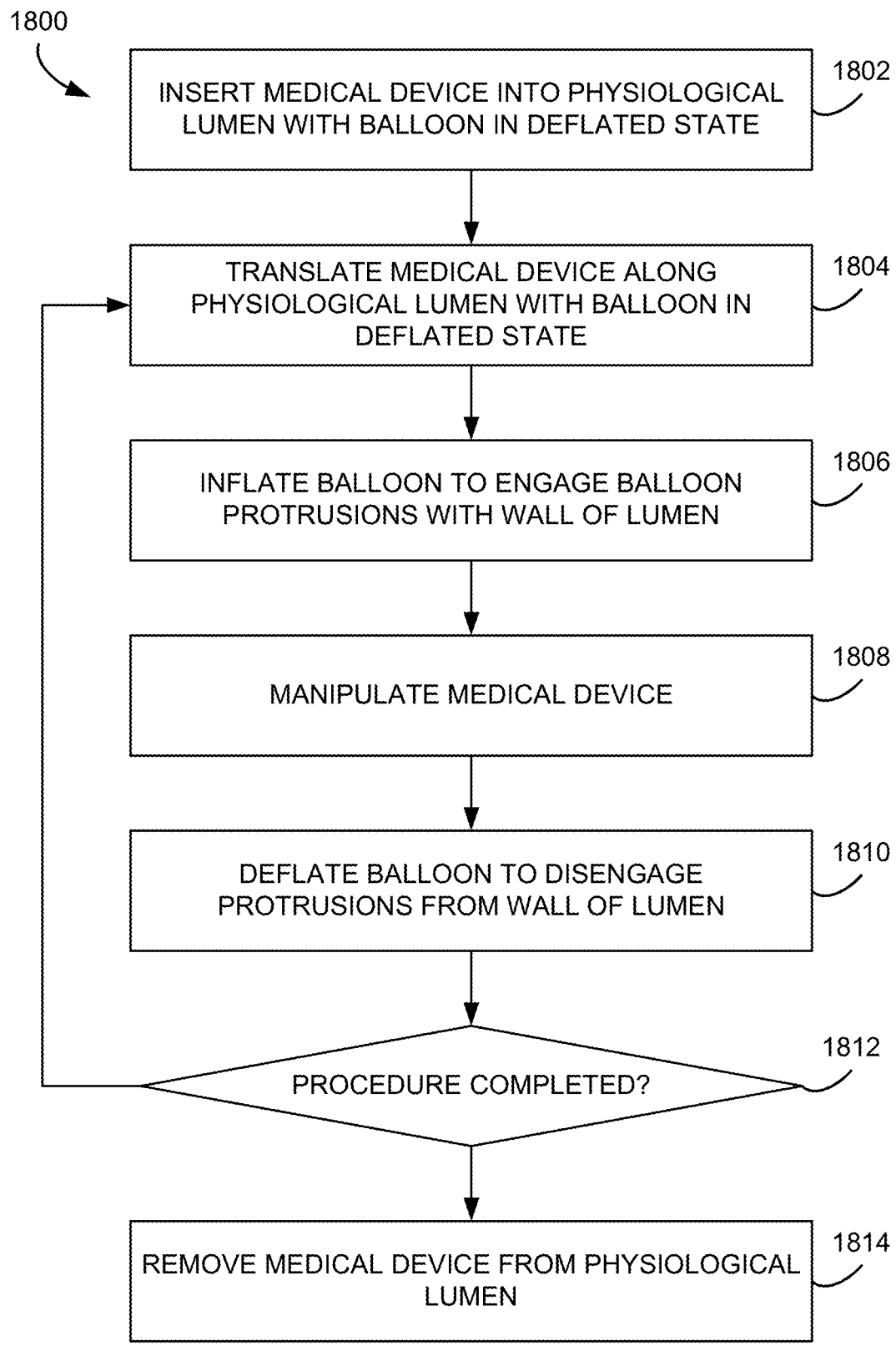
FIG. 18 is a flowchart illustrating an example method of performing a procedure using a medical device according to the present disclosure.

The current disclosure further provides methods of performing endoscopy or similar medical procedures within a body cavity. FIG. 18 is a flowchart illustrating an example method 1800 of such procedures which may be generally performed using medical devices in accordance with the present disclosure, including but not limited to the medical devices discussed in the context of FIGS. 1A-1E and 10-17.

At operation 1802, the medical device is introduced into a physiological lumen or body cavity at least with a balloon of the medical device in a deflated state. As previously discussed, in at least one application of the present disclosure, the physiological lumen may include (but is not limited to) a portion of a patient's GI tract. For example, in the context of a small bowel endoscopy, the physiological lumen may correspond to a portion of a patient's lower digestive system and the medical device may include distal components, such as a light and/or camera, adapted to facilitate examination of the physiological lumen.

Once inserted into the physiological lumen, at least a portion of the medical device is translated along the physiological lumen to an engagement location while the balloon is in the deflated state (operation 1804). For example, in certain implementations, the portion of the medical device may be a catheter including the balloon and translating the portion of the medical device may include extending the catheter and balloon along the physiological lumen while a second portion of the medical device (e.g., an endoscope body) remains at the initial insertion location. In another example implementation, translating the portion of the medical device may include moving an endoscope or similar portion of the medical device along a guide wire or catheter extending along the physiological lumen.

Following translation of the portion of the medical device, the balloon of the medical device is inflated such that protrusions of the balloon as described herein engage with the wall of the physiological lumen (operation 1806).

Once at least partially secured within the lumen, the medical device may be manipulated to perform various functions (operation 1808). In one example, the secured portion of the medical device may include a catheter and the medical device may be manipulated by translating an unsecured portion of the medical device along the physiological lumen using the secured catheter as a guide. In another implementation, the medical device may be manipulated to remove a foreign object or tissue from the physiological lumen. For example, manipulation of the medical device may include insertion and operation of one or more tools of the medical device configured to capture, excise, ablate, biopsy, or otherwise interact with tissue or objects within the physiological lumen. In one specific example, the balloon may be disposed distal a foreign object or tissue of interest within the lumen during operation 1804. The balloon may then be inflated in operation 1806 to obstruct the lumen. In one implementation, the balloon may then be moved proximally through the lumen to remove the foreign object. In another implementation, the balloon may instead be disposed within the lumen and moved distally to remove a foreign object distal the balloon. In another implementation, tools may be inserted through the medical device such that the tools may be used in a portion of the lumen proximal the inflated balloon. The foregoing examples may be useful for removing kidney stones from urinary ducts, removing gall stones from bile ducts, or clearing other foreign or undesirable matter present within the physiological lumen.

In another example medical procedure, a second balloon in accordance with the present disclosure may be disposed and inflated within the physiological lumen such that the protrusions of the second balloon partially engage the wall of the physiological lumen but otherwise remains at least partially movable within the physiological lumen. For example, the second balloon may be disposed on a guide wire or catheter that is then inserted through a medical device previously disposed within the physiological lumen (e.g., during operations 1804 and 1806). With the protrusions of the second balloon partially engaged, the second balloon may be translated along the physiological lumen to rub or scrape the wall of the physiological lumen.

Following manipulation of the medical device, the balloon is deflated to disengage the balloon from the physiological lumen (operation 1810) and an evaluation is conducted to determine when the medical procedure is complete (operation 1812). If so, the medical device is removed from the physiological lumen (operation 1814). Otherwise, the medical device may be repositioned within the physiological lumen for purposes of conducting any additional steps of the procedure (e.g., by repeating operations 1804-1812).

Figure 19:
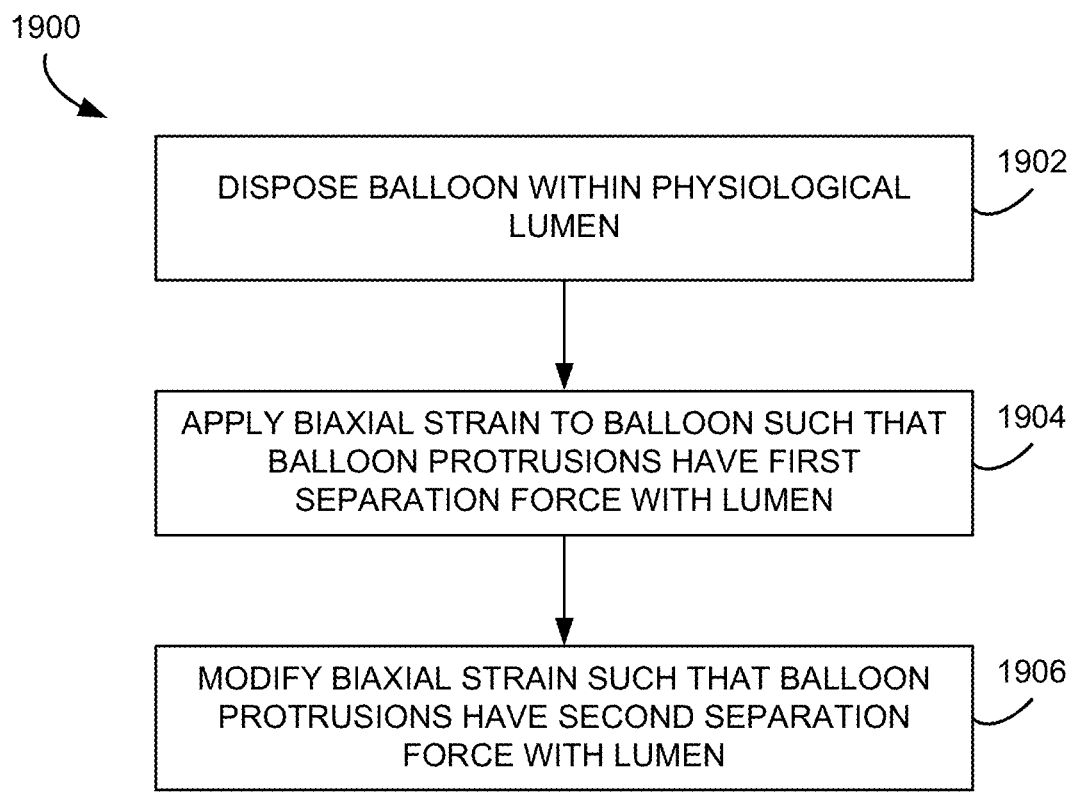
FIG. 19 is a flowchart illustrating a method of modifying engagement between a balloon in accordance with the present disclosure and a physiological lumen.

FIG. 19 is a second flowchart illustrating a method 1900 of modifying engagement between a balloon in accordance with the present disclosure and a physiological lumen. As previously discussed in the context of FIGS. 4A-7, the protrusions of balloons in accordance with the present disclosure may be configured to have adhesive and frictional properties that vary based on the biaxial strain applied to them. More specifically, applying strain to the balloon (e.g., by selectively inflating or deflating the balloon) causes deformation of the protrusions on the balloon's surface which in turn modifies adhesion and friction between the balloon and adjacent tissue. As previously discussed, by modifying the strain applied to the balloon, the adhesive and frictional properties may be dynamically manipulated by a physician to allow for improved control and flexibility during medical procedures.

With the foregoing in mind, the method 1900 begins with disposing a balloon having protrusions in accordance with the present disclosure within a physiological lumen (operation 1902). At operation 1904, a biaxial strain is applied to the balloon, such as by inflating the balloon, such that protrusions of the balloon interact with a wall of the physiological lumen and have a first separation force with the wall. At operation 1906 the biaxial strain is modified such that a second separation force different from the first separation force is achieved between the balloon and the wall of the physiological lumen.

With respect to the foregoing, modifying the biaxial strain in operation 1906 may include either of increasing or decreasing the biaxial strain on the balloon. Increasing the biaxial strain may include, for example, inflating the balloon beyond the extent to which the balloon was inflated during operation 1904. As discussed in the context of FIG. 7, increasing strain on the balloon in such a manner may generally result in an increase in the force required to separate the balloon from the wall of the physiological lumen (i.e., increase friction and/or adhesion). Decreasing the biaxial strain may include, for example, at least partially deflating the balloon to decrease the force required to separate the balloon from the wall of the physiological lumen (i.e., decrease friction and/or adhesion).

The present disclosure is further directed to kits including medical devices in accordance with the present disclosure. In certain implementations, the kit includes an endoscope or similar medical device including at least one inflatable balloon having protrusions as described herein. In other implementations, the kit further includes a catheter including a balloon having protrusions as described herein. In yet other implementations, the kit includes instructional materials detailing methods of using medical devices in accordance with the present disclosure. In still another implementation, the kit includes each of an endoscope and a catheter, each of which includes a balloon as described herein. In still other implementations, the kit includes instructional materials detailing methods of using the endoscope and the catheter.

As used herein, each of the following terms has the meaning associated with it in this section.

As used herein, unless defined otherwise, all technical and scientific terms generally have the same meaning as commonly understood by one of ordinary skill in the art to which this disclosure belongs. Generally, the nomenclature used herein is those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "instructional material" includes a publication, a recording, a diagram, or any other medium of expression that may be used to communicate the usefulness of the compositions and/or methods of the present disclosure. The instructional material of the kit may, for example, be affixed to a container that contains the compositions of the present disclosure or be shipped together with a container that contains the compositions. Alternatively, the instructional material may be shipped separately from the container with the intention that the recipient uses the instructional material and the compositions cooperatively. For example, the instructional material is for use of a kit; and/or instructions for use of the compositions.

Throughout this disclosure, various aspects of the present disclosure may be presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Every formulation or combination of components described or exemplified can be used to practice implementations of the current disclosure, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

Although the description herein contains many example implementations, these should not be construed as limiting the scope of the current disclosure but as merely providing illustrative examples.

All references throughout this disclosure (for example, patent documents including issued or granted patents or equivalents; patent application publications; and non-patent literature documents or other source material) are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. In general the terms and phrases used herein have their art-recognized meaning, which can be found by reference to standard texts, journal references, and contexts known to those skilled in the art. Any preceding definitions are provided to clarify their specific use in the context of the present disclosure.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present disclosure.

The disclosures of each and every patent, patent application, and publication cited herein are hereby incorporated herein by reference in their entirety.

While this disclosure includes reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A medical device configured to be inserted into a physiological lumen of a patient, the physiological lumen including a lumen wall, the medical device comprising:
    an elongate body;
    an inflatable balloon attached to and partially surrounding at least a section of the elongate body, the inflatable balloon being selectively inflatable between an uninflated state and an inflated state in which the inflatable balloon is strained; and
    a plurality of protrusions extending from the inflatable balloon, the plurality of protrusions configured to selectively and atraumatically engage the lumen wall;
    wherein:
        a protrusion of the plurality of protrusions extends outwardly from the inflatable balloon when the inflatable balloon is in the uninflated state, and
        the protrusion comprises an outwardly concave top surface having a first radius of curvature in the uninflated state and a second radius of curvature in the inflated state, the second radius of curvature being less than the first radius of curvature.

2. The medical device of claim 1, wherein the inflatable balloon comprises at least one material selected from the group consisting of low-density polyethylene, latex, polyether block amide, silicone, poly-siloxane, polyethylene terephthalate, nylon, and polyurethane.

3. The medical device of claim 1, wherein the protrusions have a height from and including about 300 µm to and including about 500 µm tall.

4. The medical device of claim 1, wherein the protrusions have a cross-sectional width from and including about 5 µm to and including about 700 µm.

5. The medical device of claim 4, wherein the protrusions have a cross-sectional width of about 400 µm.

6. The medical device of claim 1, wherein the protrusions have an aspect ratio up to and including about 10, the aspect ratio being a ratio between a height of the protrusions and a cross-sectional width of the protrusions.

7. The medical device of claim 6, wherein the aspect ratio is from and including 0.5 to and including 2.0.

8. The medical device of claim 1, wherein the protrusions are evenly spaced with a center-to-center spacing from and including about 20 µm to and including about 1,000 µm.

9. The medical device of claim 1, wherein the protrusions are integrally formed with the inflatable balloon.

10. The medical device of claim 1, wherein the inflatable balloon is one of a plurality of inflatable balloons distributed along a length of the medical device.

11. The medical device of claim 1, wherein the elongate body is one of an endoscope body, an endoscope overtube, a catheter, and a guide wire.

12. The medical device of claim 1, wherein, when in the uninflated state, a first portion of the inflatable balloon has a first diameter and a second portion of the inflatable balloon including at least a portion of the protrusions extends to a second diameter, the second diameter being less than the first diameter.

13. The medical device of claim 1, wherein, when in the inflated state, each of a portion of the protrusions extends in a respective first direction, and when in the uninflated state, each of the portion of the protrusions extends in a second respective direction, the first respective direction being in a more outwardly radial direction as compared to the second respective direction.

14. The medical device of claim 1, wherein each of the plurality of protrusions has a height from and including about 5 µm to and including about 1000 µm tall and a stiffness at least equal to the stiffness of the lumen wall.

15. The medical device of claim 1, wherein the protrusion has a frustoconical shape.

16. A medical device configured to be inserted into a physiological lumen of a patient, the physiological lumen including a lumen wall and formed of a lumen material, the medical device comprising:
    an elongate body; and
    an inflatable balloon attached to and partially surrounding at least a section of the elongate body, the inflatable balloon adapted to be inflated within the physiological lumen to engage with the lumen wall and to be changed from a first state to a second state by one of inflating and deflating the inflatable balloon; and
    a plurality of protrusions extending from the inflatable balloon, wherein:
        the inflatable balloon is strained in at least one of the first state and the second state,
        a protrusion of the plurality of protrusions has a top surface,
        when in the first state, the top surface has a first radius of curvature, such that when adhered to a surface formed of the lumen material, a first separation force is required to disengage the inflatable balloon from the surface,
        when in the second state, the top surface has a second radius of curvature that is different than the first radius of curvature, such that when adhered to the surface of the lumen material, a second separation force different than the first separation force is required to disengage the inflatable balloon from the surface, and
        when in the at least one of the first state and the second state, the top surface is outwardly concave.

17. The medical device of claim 16, wherein:
    when changing from the first state to the second state includes inflating the inflatable balloon, the inflatable balloon is subject to a strain in the second state, and
    when changing from the first state to the second state includes deflating the inflatable balloon, the inflatable balloon is subject to a strain in the first state.

18. The medical device of claim 16, wherein in the first state, a first strain is applied to the inflatable balloon, and in the second state, a second strain different than the first strain is applied to the inflatable balloon.

19. The medical device of claim 18, wherein at least one of the first strain and the second strain is a biaxial strain.

20. The medical device of claim 16, wherein each of the protrusions has a first shape having a first surface area when the inflatable balloon is in the first state and each of the protrusions has a second shape having a second surface area when the inflatable balloon is in the second state, the first surface area being different than the second surface area.

21. The medical device of claim 20, wherein the top surface is outwardly concave in each of the first state and the second state.

\* \* \* \* \*